US012635718B2

(12) United States Patent
Frerot et al.

(10) Patent No.: US 12,635,718 B2
(45) Date of Patent: May 26, 2026

(54) FLAVANONE DERIVATIVES AND THEIR USE AS SWEETNESS ENHANCERS

(71) Applicant: Firmenich SA, Satigny (CH)

(72) Inventors: Eric Frerot, Satigny (CH); Tim Vernet, Satigny (CH); Yves Lottaz, Satigny (CH); Kerstin Steiner, Satigny (CH); Priti Jha, Plainsboro, NJ (US); Dattatreya Banavara, Plainsboro, NJ (US)

( * ) Notice: Subject to any disclaimer, the term of this patent is extended or adjusted under 35 U.S.C. 154(b) by 677 days.

(21) Appl. No.: 17/637,944

(22) PCT Filed: Sep. 2, 2020

(86) PCT No.: PCT/EP2020/074497
§ 371 (c)(1),
(2) Date: Feb. 24, 2022

(87) PCT Pub. No.: WO2021/043842
PCT Pub. Date: Mar. 11, 2021

(65) Prior Publication Data

US 2022/0273012 A1 Sep. 1, 2022

Related U.S. Application Data

(60) Provisional application No. 62/896,017, filed on Sep. 5, 2019.

(30) Foreign Application Priority Data

Oct. 1, 2019 (EP) .................................... 19200701

(51) Int. Cl.
*A23L 27/00* (2016.01)
*A23L 2/60* (2006.01)
(Continued)

(52) U.S. Cl.
CPC ................ *A23L 27/88* (2016.08); *A23L 2/60* (2013.01); *A23L 27/30* (2016.08); *A23L 27/84* (2016.08);
(Continued)

(58) Field of Classification Search
CPC . A23L 27/88; A23L 2/60; A23L 27/30; A23L 27/84; A23L 27/86; C07D 311/32; C07D 311/62
See application file for complete search history.

(56) References Cited

U.S. PATENT DOCUMENTS 6,468,576 B1 10/2002 Sher et al.
8,076,491 B2 12/2011 Karanewsky et al.
(Continued)

FOREIGN PATENT DOCUMENTS

CN 101528059 9/2009
CN 104540396 4/2015
(Continued)

OTHER PUBLICATIONS

Apollinaire et al., vol. Nat. Prod. Lett., vol. 9, pp. 33-37 (1996).
(Continued)

*Primary Examiner* — Changqing Li
(74) *Attorney, Agent, or Firm* — Knobbe, Martens, Olson & Bear, LLP

(57) ABSTRACT

The present disclosure generally provides a class of flavanone derivatives and their use as sweetness enhancers. In some aspects, the disclosure provides certain compositions that include such flavanone derivatives, such as compositions that include such flavanone derivatives and one or more other sweeteners. In some other aspects, the disclosure provides methods of reducing the caloric content of a sweetened article, such as a sweetened food or beverage product.

4 Claims, 1 Drawing Sheet

(51) Int. Cl.
*A23L 27/30* (2016.01)
*C07D 311/62* (2006.01)

(52) U.S. Cl.
CPC ............ *A23L 27/86* (2016.08); *C07D 311/62* (2013.01); *A23V 2002/00* (2013.01)

(56) References Cited

U.S. PATENT DOCUMENTS

| | | | |
|---|---|---|---|
| 8,735,081 | B2 | 5/2014 | Li et al. |
| 8,815,956 | B2 | 8/2014 | Tachdjian et al. |
| 8,877,922 | B2 | 11/2014 | Tachdjian et al. |
| 8,968,708 | B2 | 3/2015 | Tachdjian et al. |
| 9,000,051 | B2 | 4/2015 | Feltin et al. |
| 9,000,054 | B2 | 4/2015 | Tachdjian et al. |
| 9,247,759 | B2 | 2/2016 | Karanewsky et al. |
| 9,394,287 | B2 | 7/2016 | Priest et al. |
| 9,834,544 | B2 | 12/2017 | Tachdjian et al. |
| 10,421,727 | B2 | 9/2019 | Chumakova et al. |
| 11,357,246 | B2 | 6/2022 | Patron et al. |
| 2007/0059422 | A1 | 3/2007 | Robbins |
| 2009/0111834 | A1 | 4/2009 | Tachdjian |
| 2010/0292175 | A1 | 11/2010 | Wessjohann et al. |
| 2011/0230502 | A1 | 9/2011 | Tachdjian et al. |
| 2012/0088796 | A1 | 4/2012 | Karanewsky |
| 2013/0216692 | A1 | 8/2013 | Sabater et al. |
| 2014/0342078 | A1* | 11/2014 | Hayes ........................ A23L 2/68 426/590 |
| 2014/0370177 | A1 | 12/2014 | Jia et al. |
| 2015/0050410 | A1 | 2/2015 | Luo et al. |
| 2015/0335604 | A1* | 11/2015 | Moshrefi .............. A61K 31/216 514/188 |

FOREIGN PATENT DOCUMENTS

| | | |
|---|---|---|
| WO | 88/08256 | 11/1988 |
| WO | WO 12/146584 | 11/2012 |
| WO | WO 14/153000 | 9/2014 |

OTHER PUBLICATIONS

Nanayakkara et al., J. Med. Chem., vol. 31, pp. 1250-1253 (1988).
Int'l Search Report & Written Opinion of Int'l Search Authority, PCT App. No. PCT/EP2020/074497, dated Jan. 13, 2021.

* cited by examiner

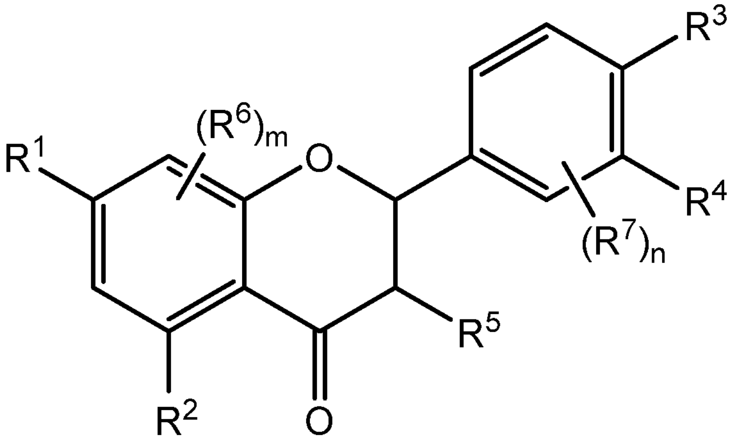

FLAVANONE DERIVATIVES AND THEIR USE AS SWEETNESS ENHANCERS

CROSS-REFERENCE TO RELATED APPLICATIONS

The present application is the United States national stage application of PCT App. No. PCT/EP2020/074497, filed Sep. 2, 2020, which claims the benefit of priority of U.S. Provisional Application No. 62/896,017, filed Sep. 5, 2019, and European Patent Application No. 19200701.1, filed Oct. 1, 2019, both of which are hereby incorporated by reference as though set forth herein in their entireties.

TECHNICAL FIELD

The present disclosure generally provides a class of flavanone derivatives and their use as sweetness enhancers. In some aspects, the disclosure provides certain compositions that include such flavanone derivatives, such as compositions that include such flavanone derivatives and one or more other sweeteners. In some other aspects, the disclosure provides methods of reducing the caloric content of a sweetened article, such as a sweetened food or beverage product.

DESCRIPTION OF RELATED ART

The taste system provides sensory information about the chemical composition of the external world. Taste transduction is one of the more sophisticated forms of chemically triggered sensation in animals. Signaling of taste is found throughout the animal kingdom, from simple metazoans to the most complex of vertebrates. Mammals are believed to have five basic taste modalities: sweet, bitter, sour, salty, and umami.

Sweetness is the taste most commonly perceived when eating foods rich in sugars. Mammals generally perceive sweetness to be a pleasurable sensation, except in excess. Caloric sweeteners, such as sucrose and fructose, are the prototypical examples of sweet substances. Although a variety of no-calorie and low-calorie substitutes exist, these caloric sweeteners are still the predominant means by which comestible products induce the perception of sweetness upon consumption.

Metabolic disorders and related conditions, such as obesity, diabetes, and cardiovascular disease, are major public health concerns throughout the world. And their prevalence is increasing at alarming rates in almost every developed country. Caloric sweeteners are a key contributor to this trend, as they are included in various packaged food and beverage products to make them more palatable to consumers. In many cases, no-calorie or low-calorie substitutes can be used in foods and beverages in place of sucrose or fructose. Even so, these compounds impart sweetness differently from caloric sweeteners, and a number of consumers fail to view them as suitable alternatives. Moreover, such compounds may be difficult to incorporate into certain products. In some instances, they may be used as partial replacements for caloric sweeteners, but their mere presence can cause many consumers to perceive unpleasant off-tastes including, astringency, bitterness, and metallic and licorice tastes. Thus, lower-calorie sweeteners face certain challenges to their adoption.

Sweetness enhancement provides an alternative approach to overcoming some of adoption challenges faced by lower-calorie sweeteners. Such compounds can be used in combination with sucrose or fructose to enhance their sweetness, thereby permitting the use of lower quantities of such caloric sweeteners in various food or beverage products. But, in addition to enhancing the perceived sweetness of the primary sweetener, such compounds nevertheless alter the perceived taste of the sweetener. Thus, many consumers find that it is less pleasurable to consume such sweetness-enhanced products in comparison to unenhanced alternatives having higher calories. Thus, there is a continuing need to discover compounds that enhance the sweetness of caloric sweeteners without altering their perceived taste in a way that detracts from the pleasure that consumers experience in eating or drinking products containing such sweeteners.

SUMMARY

The present disclosure relates to the discovery that certain compounds exhibit a desirable and surprising sweetness enhancing effect when combined with primary sweeteners at amounts effective to enhance sweetness.

In a first aspect, the disclosure provides flavor-modifying compounds, which are compounds of formula (I):

(I)

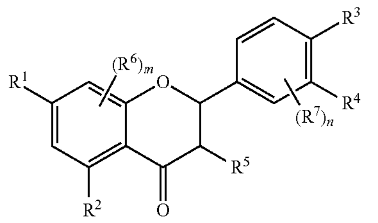

or salts thereof, wherein:

$R^1$ is a hydrogen atom, —OH, or —O—$R^{1A}$;

$R^{1A}$ is $C_{1-6}$ alkyl, which is optionally substituted one or more times by substituents selected from the group consisting of —OH and $C_{1-6}$ alkoxy; or $R^{1A}$ is a glucuronyl moiety, a furanose moiety, a pyranose moiety, or an oligosaccharide moiety having from two to five saccharide moieties, which are connected by glycosidic bonds and are selected independently from the group consisting of furanose moieties and pyranose moieties;

$R^2$ is a hydrogen atom, —OH, or —O—$R^{2A}$;

$R^{2A}$ is $C_{1-6}$ alkyl, which is optionally substituted one or more times by substituents selected from the group consisting of —OH and $C_{1-6}$ alkoxy; or $R^{2A}$ is a glucuronyl moiety, a furanose moiety, a pyranose moiety, or an oligosaccharide moiety having from two to five saccharide moieties, which are connected by glycosidic bonds and are selected independently from the group consisting of furanose moieties and pyranose moieties;

$R^3$ is —OH or —O—$R^{3A}$;

$R^{3A}$ is $C_{1-6}$ alkyl, which is optionally substituted one or more times by substituents selected from the group consisting of —OH and $C_{1-6}$ alkoxy; or $R^{3A}$ is a furanose moiety, a pyranose moiety, or an oligosaccharide moiety having from two to five saccharide moieties, which are connected by glycosidic bonds and are selected independently from the group consisting of furanose moieties and pyranose moieties;

$R^4$ is a hydrogen atom, —OH, or —O—$R^{4A}$;

$R^{4A}$ is $C_{1-6}$ alkyl, which is optionally substituted one or more times by substituents selected from the group consisting of —OH and $C_{1-6}$ alkoxy; or $R^{4A}$ is a glucuronyl moiety, a furanose moiety, a pyranose moiety, or an oligosaccharide moiety having from two to five saccharide moieties, which are connected by glycosidic bonds and are selected independently from the group consisting of furanose moieties and pyranose moieties;

$R^5$ is —OH, —O—$R^{5A}$, or —O—C(O)—$R^{5B}$;

$R^{5A}$ is $C_{1-6}$ alkyl, which is optionally substituted one or more times by substituents selected from the group consisting of —OH and $C_{1-6}$ alkoxy; or $R^{5A}$ is a glucuronyl moiety, a furanose moiety, a pyranose moiety, or an oligosaccharide moiety having from two to five saccharide moieties, which are connected by glycosidic bonds and are selected independently from the group consisting of furanose moieties and pyranose moieties;

$R^{5B}$ is —H or $C_{1-6}$ alkyl, which is optionally substituted one or more times by substituents selected from the group consisting of —OH and $C_{1-6}$ alkoxy;

$R^6$ and $R^7$ are independently selected from the group consisting of $C_{1-6}$ alkyl, —OH, $C_{1-6}$ alkoxy, and —O—($C_{1-6}$ alkylene)-O—($C_{1-6}$alkyl);

m is 0, 1, or 2; and n is 0, 1, 2, or 3.

In a second and related aspect, the disclosure provides a flavor-modifying compound, which is a compound of formula (Ia)

(Ia)

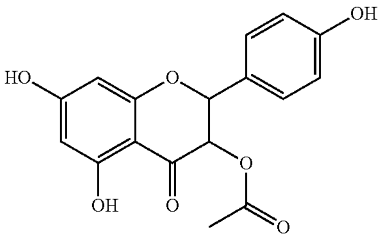

or a salt thereof.

In a third and related aspect, the disclosure provides a flavor-modifying compound, which is a compound of formula (Ic)

(Ic)

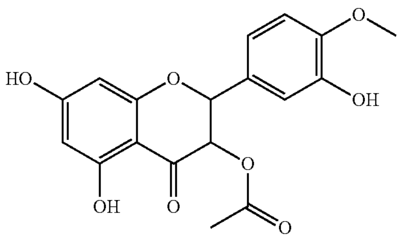

or a salt thereof.

In a fourth aspect, the disclosure provides uses of any flavor-modifying compounds of the first through the third aspects.

In a fifth aspect, the disclosure provides uses of any flavor-modifying compounds of the first through the third aspects to enhance the sweetness of an ingestible composition. In some embodiments thereof, the ingestible composition comprises a caloric sweetener. In some other embodiments thereof, the ingestible composition comprises a non-caloric sweetener. In some embodiments, the sweetener is a high-intensity sweetener.

In a sixth aspect, the disclosure provides uses of any flavor-modifying compounds of the first through the third aspects to reduce the sourness of an ingestible composition.

In a seventh aspect, the disclosure provides uses of any flavor-modifying compounds of the first through the third aspects to reduce the bitterness of an ingestible composition.

In an eighth aspect, the disclosure provides uses of any flavor-modifying compounds of the first through the third aspects in the manufacture of an ingestible composition to enhance the sweetness of the ingestible composition. In some embodiments thereof, the ingestible composition comprises a caloric sweetener. In some other embodiments thereof, the ingestible composition comprises a non-caloric sweetener. In some embodiments, the sweetener is a high-intensity sweetener.

In a ninth aspect, the disclosure provides uses of any flavor-modifying compounds of the first through the third aspects in the manufacture of an ingestible composition to reduce the sourness of the ingestible composition.

In a tenth aspect, the disclosure provides uses of any flavor-modifying compounds of the first through the third aspects in the manufacture of an ingestible composition to reduce the bitterness of the ingestible composition.

In an eleventh aspect, the disclosure provides methods of enhancing the sweetness of an ingestible composition, comprising introducing an amount (such as a sweetness-enhancing effective amount) of any compounds of the first through the third aspects to the ingestible composition.

In a twelfth aspect, the disclosure provides methods of reducing the sourness of an ingestible composition, comprising introducing an amount (such as a sourness-reducing effective amount) of any compounds of the first through the third aspects to the ingestible composition.

In a thirteenth aspect, the disclosure provides methods of reducing the bitterness of an ingestible composition, comprising introducing an amount (such as a bitterness-reducing effective amount) of any compounds of the first through the third aspects to the ingestible composition.

In a fourteenth aspect, the disclosure provides compositions comprising any compounds of the first through the third aspects, wherein the compounds of the first through the third aspects make up at least 50% by weight of the compositions on a dry weight basis (e.g., based on the total weight of the composition excluding the weight of any liquid carrier).

In a fifteenth aspect, the disclosure provides solid-state compositions comprising any compounds of the first through the third aspects, wherein the compounds of the first through the third aspects make up at least 50% by weight of the solid-state compositions, based on the total weight of composition.

In a sixteenth aspect, the disclosure provides ingestible compositions comprising any compounds of the first through the third aspects, wherein the concentration of the compounds of the first through the third aspects in the ingestible compositions is no more than 200 ppm.

In a seventeenth aspect, the disclosure provides ingestible compositions comprising any compounds of the first through the third aspects, wherein the ingestible compositions comprise no more than 1000 ppm of steviol glycosides, mogrosides, or functionalized derivatives thereof (including chemically or enzymatically functionalized derivatives). In some further embodiments, the ingestible compositions comprise no more than 1000 ppm of steviol glycosides.

In an eighteenth aspect, the disclosure provides ingestible compositions comprising any compounds of the first through the third aspects, wherein the ingestible compositions comprise a caloric sweetener, such as sucrose, fructose, glucose, xylitol, erythritol, or combinations thereof.

In a nineteenth aspect, the disclosure provides a concentrated sweetening composition comprising any compounds of the first through the third aspects and a sweetener.

In a twentieth aspect, the disclosure provides flavored products comprising any compositions of the preceding five aspects. In some embodiments, the flavored products are beverage products, such as soda, flavored water, tea, and the like. In some other embodiments, the flavored products are food products, such as yogurt.

In a twenty-first aspect, the disclosure provides methods of making compounds of the first through the third aspects, comprising: providing a flavanone, which is unsubstituted at the 3-position; and contacting the flavanone with an enzyme to functionalize the flavanone at the 3-position. In some embodiments, further functionalization is carried out.

Further aspects, and embodiments thereof, are set forth below in the Detailed Description, the Drawings, the Abstract, and the Claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

FIG. 1 shows a chemical formula that represents non-limiting examples of compounds (or salts thereof) disclosed herein, wherein: $R^1$ and $R^2$ are independently a hydrogen atom, hydroxyl, optionally substituted alkoxy, glucuronate, or saccharidyloxy (such as a monosaccharide, disaccharide, trisaccharide, etc., comprising furanose or pyranose moieties and connected to flavanone core structure via a glycosidic linkage); $R^3$ is hydroxyl, optionally substituted alkoxy, glucuronate, or saccharidyloxy (such as described above for $R^1$ and $R^2$); $R^4$ is a hydrogen atom, hydroxyl, optionally substituted alkoxy, glucuronate, or saccharidyloxy (such as described above for $R^1$ and $R^2$); $R^5$ is hydroxyl, optionally substituted alkoxy, glucuronate, formyloxy, or optionally substituted alkanoyloxy; and $R^6$ and $R^7$ are optionally present substituents.

DETAILED DESCRIPTION

The following Detailed Description sets forth various aspects and embodiments provided herein. The description is to be read from the perspective of the person of ordinary skill in the relevant art. Therefore, information that is well known to such ordinarily skilled artisans is not necessarily included.

Definitions

The following terms and phrases have the meanings indicated below, unless otherwise provided herein. This disclosure may employ other terms and phrases not expressly defined herein. Such other terms and phrases have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary As used herein, "solvate" means a compound formed by the interaction of one or more solvent molecules and one or more compounds described herein. In some embodiments, the solvates are ingestibly acceptable solvates, such as hydrates.

As used herein, "$C_a$ to $C_b$" or "$C_{a-b}$" in which "a" and "b" are integers, refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, "halogen" or "halo" means any one of the radio-stable atoms of column 7 of the Periodic Table of the Elements, such as fluorine, chlorine, bromine, or iodine. In some embodiments, "halogen" or "halo" refer to fluorine or chlorine.

As used herein, "alkyl" means a straight or branched hydrocarbon chain that is fully saturated (i.e., contains no double or triple bonds). In some embodiments, an alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. Unless indicated to the contrary, the term "alkyl" refers to a group that is not further substituted.

As used herein, "substituted alkyl" means an alkyl group substituted with one or more substituents independently selected from $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (═O).

As used herein, "alkoxy" means a moiety of the formula —OR wherein R is an alkyl, as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" means a moiety of the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" means a straight or branched hydrocarbon chain containing one or more double bonds. In some embodiments, the alkenyl group has from 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. Unless indicated to the contrary, the term "alkenyl" refers to a group that is not further substituted.

As used herein, "alkynyl" means a straight or branched hydrocarbon chain containing one or more triple bonds. In some embodiments, the alkynyl group has from 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl.

Typical alkynyl groups include, but are in no way limited to, ethynyl, propynyl, butynyl, pentynyl, and hexynyl, and the like. Unless indicated to the contrary, the term "alkynyl" refers to a group that is not further substituted.

As used herein, "heteroalkyl" means a straight or branched hydrocarbon chain containing one or more heteroatoms, that is, an element other than carbon, including but not limited to, nitrogen, oxygen, and sulfur, in the chain backbone. In some embodiments, the heteroalkyl group has from 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain. Unless indicated to the contrary, the term "heteroalkyl" refers to a group that is not further substituted.

As used herein, "alkylene" means a branched or straight chain fully saturated di-radical chemical group containing only carbon and hydrogen that is attached to the rest of the molecule via two points of attachment (i.e., an alkanediyl). In some embodiments, the alkylene group has from 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene. Unless indicated to the contrary, the term "alkylene" refers to a group that is not further substituted.

As used herein, "alkenylene" means a straight or branched chain di-radical chemical group containing only carbon and hydrogen and containing at least one carbon-carbon double bond that is attached to the rest of the molecule via two points of attachment. In some embodiments, the alkenylene group has from 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl. Unless indicated to the contrary, the term "alkenylene" refers to a group that is not further substituted.

As used herein, "aromatic" means a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" means an aromatic ring or ring system (i.e., two or more fused rings that share two adjacent carbon atoms) containing only carbon in the ring backbone.

When the aryl is a ring system, every ring in the system is aromatic. In some embodiments, the aryl group has from 6 to 18 carbon atoms, although the present definition also covers the occurrence of the term "aryl" where no numerical range is designated. In some embodiments, the aryl group has from 6 to 10 carbon atoms. The aryl group may be designated as "$C_{6-10}$ aryl," "$C_6$-$C_{10}$ aryl," or similar designations. Examples of aryl groups include, but are not limited to, phenyl, naphthyl, azulenyl, and anthracenyl. In some embodiments, the term "aryl" refers to phenyl. Unless indicated to the contrary, the term "aryl" refers to a group that is not further substituted As used herein, "aryloxy" and "arylthio" mean moieties of the formulas RO- and RS-, respectively, in which R is an aryl as is defined above, such as "$C_{6-10}$ aryloxy" or "$C_{6-10}$ arylthio" and the like, including but not limited to phenyloxy and phenylthio.

As used herein "aralkyl" or "arylalkyl" means an aryl group connected, as a substituent, via an alkylene group, such as "$C_{7-14}$ aralkyl" and the like, including, but not limited to, benzyl, 2-phenylethyl, 3-phenylpropyl, and the like. In some embodiments, the alkylene group is a lower alkylene group (i.e., a $C_{1-4}$ alkylene group).

As used herein, "heteroaryl" means an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. In some embodiments, the heteroaryl group has from 5 to 18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has from 5 to 10 ring members or from 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl. Unless indicated to the contrary, the term "hereoaryl" refers to a group that is not further substituted.

As used herein, "heteroaralkyl" or "heteroarylalkyl" means heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. In some embodiments, the carbocyclyl group has from 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro [4.4]nonanyl. Unless indicated to the contrary, the term "carbocyclyl" refers to a group that is not further substituted.

As used herein, "(carbocyclyl)alkyl" means a carbocyclyl group connected, as a substituent, via an alkylene group, such as "$C_{4-10}$(carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system, according to any of the embodiments set forth above for carbocyclyl. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic, and according to any of the embodiments set forth above for carbocyclyl. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. In some embodiments, the heterocyclyl group has from 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "(heterocyclyl)alkyl" means a heterocyclyl group connected, as a substituent, via an alkylene group. Examples include, but are not limited to, imidazolinylmethyl and indolinylethyl.

An "acyl" group refers to a —C(=O)R, wherein R is hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "sulfonyl" group refers to an "—$SO_2R$" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-sulfonamido" group refers to a "—$N(R_A)SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-carbamyl" group refers to a "—$OC(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-carbamyl" group refers to an "—$N(R_A)C(=O)OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "O-thiocarbamyl" group refers to a "—$OC(=S)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-thiocarbamyl" group refers to an "—$N(R_A)C(=S)OR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

A "C-amido" group refers to a "—$C(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "N-amido" group refers to a "—$N(R_A)C(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 3-10 membered heterocycyl, as defined herein. A non-limiting example includes free amino (i.e., —$NH_2$).

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a "glucosyl moiety" is a monovalent moiety in which one of the hydroxyl groups of glucose is replaced by a bond to another atom, functional group, or moiety. Unless otherwise specified, the glucose can have any suitable stereochemistry.

Thus, the term includes moieties having D stereochemistry, as well as moieties having L stereochemistry. Further, the term includes moieties having a stereochemistry, as well as moieties having β stereochemistry. The carbon atoms of the glucosyl moiety follow the conventional numbering, as shown below. The diagram is shown for β-D glucose, but applies in an analogous way to glucosyl moieties having α and/or L stereochemistry:

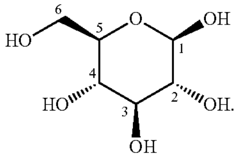

As used herein, a "glucuronyl moiety" is a monovalent moiety in which one of the hydroxyl groups of glucuronic acid is replaced by a bond to another atom, functional group, or moiety. Unless otherwise specified, the glucuronic acid can have any suitable stereochemistry. Thus, the term includes moieties having D stereochemistry, as well as moieties having L stereochemistry. Further, the term includes moieties having α stereochemistry, as well as moieties having β stereochemistry. The carbon atoms of the gluruconyl moiety follow the conventional numbering, as shown below. The diagram is shown for β-D glucuronic acid, but applies in an analogous way to glucuronyl moieties having a and/or L stereochemistry:

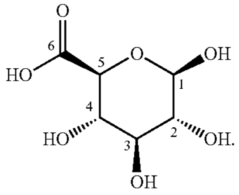 [SMILES: O=C(O)[C@H]1O[C@@H](O)[C@H](O)[C@@H](O)[C@@H]1O]

The term "$C_{1-6}$ alkyl glucuronyl ester moiety" refers to a glucuronyl moiety (as defined in this paragraph) in which the carboxylic acid group of glucuronic acid has a $C_{1-6}$ alkyl group in place of the hydrogen atom of the carboxylic acid group. In any of the embodiments below, the $C_{1-6}$ alkyl moiety can have any suitable value, such as methyl, ethyl, isopropyl, propyl, butyl, pentyl, and the like. In some embodiments, the $C_{1-6}$alkyl moiety is methyl. In some other embodiments, the $C_{1-6}$ alkyl moiety is ethyl.

As used herein, a substituted group is derived from the unsubstituted parent group in which there has been an exchange of one or more hydrogen atoms for another atom or group.

Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyloxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$—C(alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-thio (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (═O). Wherever a group is described as "optionally substituted" that group can be substituted with the above substituents.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

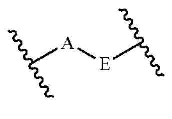

includes the substituent being oriented such that the A is attached at the leftmost attachment point of the molecule as well as the case in which A is attached at the rightmost attachment point of the molecule.

A "sweetener", "sweet flavoring agent", "sweet flavor entity", or "sweet compound" herein refers to a compound or ingestibly acceptable salt thereof that elicits a detectable sweet flavor in a subject, e.g., a compound that activates a T1R2/T1R3 receptor in vitro.

As used herein, the singular forms "a," "an," and "the" include plural referents unless the context clearly dictates otherwise. For example, reference to “a substituent” encompasses a single substituent as well as two or more substituents, and the like.

As used herein, “for example,” “for instance,” “such as,” or “including” are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, “comprise” or “comprises” or “comprising” or “comprised of” refer to groups that are open, meaning that the group can include additional members in addition to those expressly recited. For example, the phrase, “comprises A” means that A must be present, but that other members can be present too. The terms “include,” “have,” and “composed of” and their grammatical variants have the same meaning. In contrast, “consist of” or “consists of” or “consisting of” refer to groups that are closed. For example, the phrase “consists of A” means that A and only A is present.

As used herein, “optionally” means that the subsequently described event(s) may or may not occur. In some embodiments, the optional event does not occur. In some other embodiments, the optional event does occur one or more times.

As used herein, “or” is to be given its broadest reasonable interpretation, and is not to be limited to an either/or construction. Thus, the phrase “comprising A or B” means that A can be present and not B, or that B is present and not A, or that A and B are both present. Further, if A, for example, defines a class that can have multiple members, e.g., $A_1$ and $A_2$, then one or more members of the class can be present concurrently.

As used herein, the term “flavor-modifying compound(s)” refers to compounds of formula (I) or salts thereof, or any embodiments thereof set forth herein. For example, in come instances, the term “flavor-modifying compound(s)” refers to compounds of formula (Ia). In some instances, the term “flavor-modifying compound(s)” refers to compounds of formula (Ib). In some instances, the term “flavor-modifying compound(s)” refers to compounds of formula (Ic). In some instances, the term “flavor-modifying compound(s)” refers to compounds of formula (Id).

As used herein, certain substituents or linking groups having only a single atom may be referred to by the name of the atom. For example, in some cases, the substituent “—H” may be referred to as “hydrogen” or “a hydrogen atom,” the substituent “—F” may be referred to as “fluorine” or “a fluorine atom,” and the linking group “—O—” may be referred to as “oxygen” or “an oxygen atom.”

Points of attachment for groups are generally indicated by a terminal dash (-) or by an asterisk (*). For example, a group such as *—$CH_2$—$CH_3$ or —$CH_2$—$CH_3$ both represent an ethyl group.

Chemical structures are often shown using the “skeletal” format, such that carbon atoms are not explicitly shown, and hydrogen atoms attached to carbon atoms are omitted entirely. For example, the structure

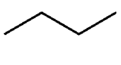

represents butane (i.e., n-butane). Furthermore, aromatic groups, such as benzene, are represented by showing one of the contributing resonance structures. For example, the structure

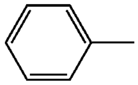

represents toluene.

Positions on the flavanone ring may be referred to by a number, such as the “2-position,” the “3-position,” and the like. These terms refer to specific positions on the fused ring structure of flavanone, even if further substitution of the fused ring structure may otherwise cause the positions to be numbered differently. Thus, for example, the carbonyl-substituted position is referred to as occurring at the “4-position” regardless of whether, in some embodiments, the addition of further substituents would cause it to occur at something besides the 4-position on the fused ring structure. Likewise, the position of the substituted phenyl substituent on the fused ring structure is referred to as occurring at the “2-position” regardless of whether, in some embodiments, the addition of further substituents would cause it to occur at something besides the 2-position on the fused ring structure.

Other terms are defined in other portions of this description, even though not included in this subsection.

Flavanone Derivatives

In a first aspect, the disclosure provides flavor-modifying compounds, which are compounds of formula (I):

(I)

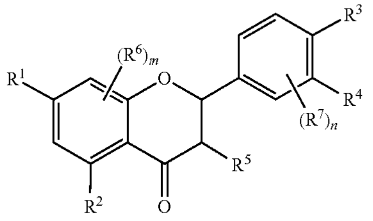

or salts thereof, wherein:

$R^1$ is a hydrogen atom, —OH, or —O—$R^{1A}$;

$R^{1A}$ is $C_{1-6}$ alkyl, which is optionally substituted one or more times by substituents selected from the group consisting of —OH and $C_{1-6}$ alkoxy; or $R^{1A}$ is a glucuronyl moiety, a furanose moiety, a pyranose moiety, or an oligosaccharide moiety having from two to five saccharide moieties, which are connected by glycosidic bonds and are selected independently from the group consisting of furanose moieties and pyranose moieties;

$R^2$ is a hydrogen atom, —OH, or —O—$R^{2A}$;

$R^{2A}$ is $C_{1-6}$ alkyl, which is optionally substituted one or more times by substituents selected from the group consisting of —OH and $C_{1-6}$ alkoxy; or $R^{2A}$ is a glucuronyl moiety, a furanose moiety, a pyranose moiety, or an oligosaccharide moiety having from two to five saccharide moieties, which are connected by glycosidic bonds and are selected independently from the group consisting of furanose moieties and pyranose moieties;

$R^3$ is —OH or —O—$R^{3A}$;

$R^{3A}$ is $C_{1-6}$ alkyl, which is optionally substituted one or more times by substituents selected from the group consisting of —OH and $C_{1-6}$ alkoxy; or $R^{3A}$ is a glucuronyl moiety, a furanose moiety, a pyranose moiety, or an oligosaccharide moiety having from two to five saccharide moieties, which are connected by glycosidic bonds and are selected independently from the group consisting of furanose moieties and pyranose moieties;

$R^4$ is a hydrogen atom, —OH, or —O—$R^{4A}$;

$R^{4A}$ is $C_{1-6}$ alkyl, which is optionally substituted one or more times by substituents selected from the group consisting of —OH and $C_{1-6}$ alkoxy; or $R^{4A}$ is a glucuronyl moiety, a furanose moiety, a pyranose moiety, or an oligosaccharide moiety having from two to five saccharide moieties, which are connected by glycosidic bonds and are selected independently from the group consisting of furanose moieties and pyranose moieties;

$R^5$ is —OH, —O—$R^{5A}$, or —O—C(O)—$R^{5B}$;

$R^{5A}$ is $C_{1-6}$ alkyl, which is optionally substituted one or more times by substituents selected from the group consisting of —OH and $C_{1-6}$ alkoxy; or $R^{5A}$ is a glucuronyl moiety, a furanose moiety, a pyranose moiety, or an oligosaccharide moiety having from two to five saccharide moieties, which are connected by glycosidic bonds and are selected independently from the group consisting of furanose moieties and pyranose moieties;

$R^{5B}$ is —H or $C_{1-6}$ alkyl, which is optionally substituted one or more times by substituents selected from the group consisting of —OH and $C_{1-6}$ alkoxy;

$R^6$ and $R^7$ are independently selected from the group consisting of $C_{1-6}$ alkyl, —OH, $C_{1-6}$ alkoxy, and —O—($C_{1-6}$ alkylene)-O—($C_{1-6}$alkyl);

m is 0, 1, or 2; and n is 0, 1, 2, or 3.

Various embodiments of the foregoing aspect are also contemplated as part of the present disclosure. Those embodiments are set forth below, and throughout other portions of the Detailed Description.

In some embodiments of the first aspect, $R^1$ is a hydrogen atom. In some other embodiments, $R^1$ is —OH. In some other embodiments, $R^1$ is —O—$R^{1A}$. In some further such embodiments of any of the foregoing embodiments, $R^{1A}$ is $C_{1-6}$ alkyl, which is optionally substituted as set forth above. In some other embodiments, $R^{1A}$ is unsubstituted $C_{1-6}$ alkyl, such as methyl, ethyl, or isopropyl. In some embodiments, $R^{1A}$ is methyl. In some other embodiments, $R^{1A}$ is a glucuronyl moiety. In some other embodiments, $R^{1A}$ is a furanose moiety or a pyranose moiety, such as a glucosidyl moiety. In some other embodiments, $R^{1A}$ is an oligosaccharide moiety, as described above, such as a diglucosidyl moiety, a triglucosidyl moiety, a tetraglucosidyl moiety, or a pentaglucosidyl moiety.

In some embodiments of any of the foregoing embodiments, $R^2$ is a hydrogen atom. In some other embodiments, $R^2$ is —OH. In some other embodiments of any of the foregoing embodiments, $R^2$ is —O—$R^{2A}$. In some further such embodiments, $R^{2A}$ is $C_{1-6}$ alkyl, which is optionally substituted as set forth above. In some other embodiments, $R^{2A}$ is unsubstituted $C_{1-6}$ alkyl, such as methyl, ethyl, or isopropyl. In some embodiments, $R^{2A}$ is methyl. In some other embodiments, $R^{2A}$ is a glucuronyl moiety. In some other embodiments, $R^{2A}$ is a furanose moiety or a pyranose moiety, such as a glucosidyl moiety. In some other embodiments, $R^{2A}$ is an oligosaccharide moiety, as described above, such as a diglucosidyl moiety, a triglucosidyl moiety, a tetraglucosidyl moiety, or a pentaglucosidyl moiety.

In some embodiments of any of the foregoing embodiments, $R^3$ is —OH. In some other embodiments of any of the foregoing embodiments, $R^3$ is —O—$R^{3A}$. In some further such embodiments, $R^{3A}$ is $C_{1-6}$ alkyl, which is optionally substituted as set forth above. In some other embodiments, $R^{3A}$ is unsubstituted $C_{1-6}$ alkyl, such as methyl, ethyl, or isopropyl. In some embodiments, $R^{3A}$ is methyl. In some other embodiments, $R^{3A}$ is a glucuronyl moiety. In some other embodiments, $R^{3A}$ is a furanose moiety or a pyranose moiety, such as a glucosidyl moiety. In some other embodiments, $R^{3A}$ is an oligosaccharide moiety, as described above, such as a diglucosidyl moiety, a triglucosidyl moiety, a tetraglucosidyl moiety, or a pentaglucosidyl moiety.

In some embodiments of any of the foregoing embodiments, $R^4$ is a hydrogen atom. In some other embodiments of any of the foregoing embodiments, $R^4$ is —OH. In some other embodiments of any of the foregoing embodiments, $R^4$ is —O—$R^{4A}$. In some further such embodiments, $R^{4A}$ is $C_{1-6}$alkyl, which is optionally substituted as set forth above. In some other embodiments, $R^{4A}$ is unsubstituted $C_{1-6}$ alkyl, such as methyl, ethyl, or isopropyl. In some embodiments, $R^{4A}$ is methyl. In some other embodiments, $R^{4A}$ is a glucuronyl moiety. In some other embodiments, $R^{4A}$ is a furanose moiety or a pyranose moiety, such as a glucosidyl moiety. In some other embodiments, $R^{4A}$ is an oligosaccharide moiety, as described above, such as a diglucosidyl moiety, a triglucosidyl moiety, a tetraglucosidyl moiety, or a pentaglucosidyl moiety.

In some embodiments of any of the foregoing embodiments, $R^5$ is —OH. In some other embodiments of any of the foregoing embodiments, $R^5$ is —O—$R^{5A}$. In some further such embodiments, $R^{5A}$ is $C_{1-6}$alkyl, which is optionally substituted as set forth above. In some other embodiments, $R^{5A}$ is unsubstituted $C_{1-6}$ alkyl, such as methyl, ethyl, or isopropyl. In some embodiments, $R^{5A}$ is methyl. In some other embodiments, $R^{5A}$ is a glucuronyl moiety.

In some other embodiments, $R^{5A}$ is a furanose moiety or a pyranose moiety, such as a glucosidyl moiety. In some other embodiments, $R^{5A}$ is an oligosaccharide moiety, as described above, such as a diglucosidyl moiety, a triglucosidyl moiety, a tetraglucosidyl moiety, or a pentaglucosidyl moiety. In some other embodiments of any of the foregoing embodiments, $R^5$ is —O—C(O)—$R^{5B}$. In some further such embodiments, $R^{5B}$ is $C_{1-6}$alkyl, which is optionally substituted as set forth above. In some other embodiments, $R^{5B}$ is unsubstituted $C_{1-6}$ alkyl, such as methyl, ethyl, or isopropyl. In some embodiments, $R^{5B}$ is methyl. In some other such embodiments, $R^{5B}$ is a hydrogen atom.

The variables m and n can have any suitable value within the limits set forth above. In some embodiments of any of the foregoing embodiments, m is 0. In some other embodiments of any of the foregoing embodiments, m is 1. In some embodiments of any of the foregoing embodiments, n is 0. In some other embodiments of any of the foregoing embodiments, n is 1. Note that $R^6$ refers to non-hydrogen substituents that are optionally present at the two positions on the phenyl portion of the bicyclic ring system, which represent the 6-position and the 8-position, according to the traditional numbering for flavanone. Thus, when m is zero, the substituent at both of those positions is a hydrogen atom. When m is one, then there is a non-hydrogen substituent at one of the two positions, selected from the variables set forth in the definition of $R^6$. And when m is two, there is a non-hydrogen substituent at both positions. In an analogous way, $R^7$ refers to hon-hydrogen substituents that are optionally present at the three positions on the phenyl ring that is attached at the 2-position of the bicyclic ring (according to the traditional numbering of positions for flavanone). Thus, when n is zero, the substituent at those three positions (i.e., the three positions besides those occupied by $R^3$ and $R^4$) is a hydrogen atom. And when n is one, there is a non-hydrogen substituent at one of those three available positions. And when n is two, there is a non-hydrogen substituent at two of those three available positions. And when n is three, there is a non-hydrogen substituent at each of those three available positions.

In some embodiments of any of the foregoing embodiments, $R^1$ and $R^2$ are —OH, $R^3$ is —OH or —$OCH_3$, and $R^4$ is —H or —OH, and $R^5$ is —O—C(O)—$CH_3$, and $R^6$ and $R^7$ are —H.

In a related aspect, the disclosure provides a flavor-modifying compound, which is a compound of formula (Ia)

(Ia)

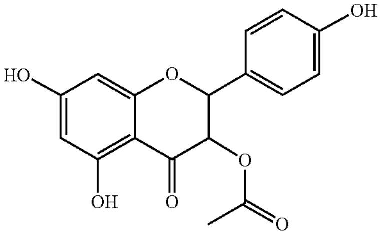

or a salt thereof. In some embodiments thereof, the compound exists as a mixture of any two or more, any three or more, or all four of the stereoisomers encompassed by the structure, i.e., (2R,3R), (2R,3S), (2S,3R), and (2S,3S). In some further embodiments, the compound exists in substantially pure form of one of the four stereoisomers, i.e., a purity of 95% or more, or 97% or more, 98% or more, or 99% or more, or 99.5% or more, or 99.7% or more, or 99.9% or more.

In some further embodiments thereof, the flavor-modifying compound is a compound of formula (Ib)

(Ib)

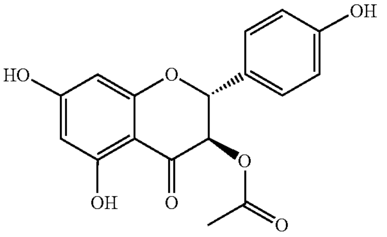

or a salt thereof.

In a related aspect, the disclosure provides a flavor-modifying compound, which is a compound of formula (Ic)

(Ic)

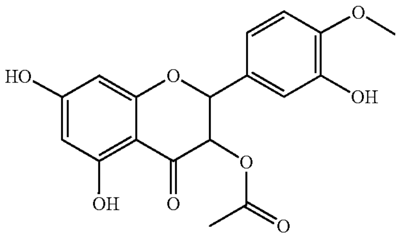

or a salt thereof. In some embodiments thereof, the compound exists as a mixture of any two or more, any three or more, or all four of the stereoisomers encompassed by the structure, i.e., (2R,3R), (2R,3S), (2S,3R), and (2S,3S). In some further embodiments, the compound exists in substantially pure form of one of the four stereoisomers, i.e., a purity of 95% or more, or 97% or more, 98% or more, or 99% or more, or 99.5% or more, or 99.7% or more, or 99.9% or more.

In some further embodiments thereof, the flavor-modifying compound is a compound of formula (Id)

(Id)

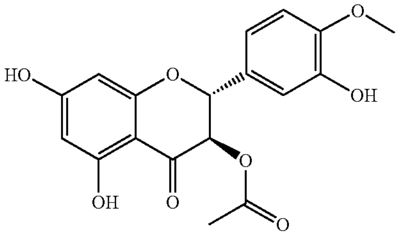

or a salt thereof.

Where the compounds disclosed herein have at least one chiral center, they may exist as individual enantiomers and diastereomers or as mixtures of such isomers. In some embodiments in connection with the second aspect, the sweet-enhancing compound has substantial enantiomeric purity.

For example, in some embodiments, a composition comprising the compound of formula (Ia), or a salt thereof, the (2R,3R) enantiomer makes up at least 50% by weight, or at least 60% by weight, or at least 70% by weight, or at least 80% by weight, or at least 90% by weight, or at least 95% by weight, or at least 97% by weight, or at least 99% by weight, of the amount of compound present in the composition, based on the total weight of the compound [i.e., amount of (2R,3R)+amount of (2S,3R)+amount of (2R,3S)+amount of (2S,3S)] in the composition. In some other embodiments, a composition comprising the compound of formula (Ia), or a salt thereof, the (2R,3S) enantiomer makes up at least 50% by weight, or at least 60% by weight, or at least 70% by weight, or at least 80% by weight, or at least 90% by weight, or at least 95% by weight, or at least 97% by weight, or at least 99% by weight, of the amount of compound present in the composition, based on the total weight of the compound in the composition. In some other embodiments, a composition comprising the compound of formula (Ia), or a salt thereof, the (2S,3R) enantiomer makes up at least 50% by weight, or at least 60% by weight, or at least 70% by weight, or at least 80% by weight, or at least 90% by weight, or at least 95% by weight, or at least 97% by weight, or at least 99% by weight, of the amount of compound present in the composition, based on the total weight of the compound in the composition. In some other embodiments, a composition comprising the compound of formula (Ia), or a salt thereof, the (2S,3S) enantiomer makes up at least 50% by weight, or at least 60% by weight, or at least 70% by weight, or at least 80% by weight, or at least 90% by weight, or at least 95% by weight, or at least 97% by weight, or at least 99% by weight, of the amount of compound present in the composition, based on the total weight of the compound in the composition.

In some other embodiments of any of the embodiments of the preceding paragraph, a composition comprising the compound of formula (Ia), or a salt thereof, the (2R,3R) enantiomer makes up no more than 50% by weight, or no more than 40% by weight, or no more than 30% by weight, or no more than 20% by weight, or no more than 10% by weight, or no more than 5% by weight, or no more than 3% by weight, or no more than 1% by weight, of the amount of compound present in the composition, based on the total weight of the compound in the composition. In some other embodiments of any of the embodiments of the preceding paragraph, a composition comprising the compound of formula (Ia), or a salt thereof, the (2R,3S) enantiomer makes up no more than 50% by weight, or no more than 40% by weight, or no more than 30% by weight, or no more than 20% by weight, or no more than 10% by weight, or no more than 5% by weight, or no more than 3% by weight, or no more than 1% by weight, of the amount of compound present in the composition, based on the total weight of the compound in the composition. In some other embodiments of any of the embodiments of the preceding paragraph, a composition comprising the compound of formula (Ia), or a salt thereof, the (2S,3R) enantiomer makes up no more than 50% by weight, or no more than 40% by weight, or no more than 30% by weight, or no more than 20% by weight, or no more than 10% by weight, or no more than 5% by weight, or no more than 3% by weight, or no more than 1% by weight, of the amount of compound present in the composition, based on the total weight of the compound in the composition. In some other embodiments of any of the embodiments of the preceding paragraph, a composition comprising the compound of formula (Ia), or a salt thereof, the (2S,3S) enantiomer makes up no more than 50% by weight, or no more than 40% by weight, or no more than 30% by weight, or no more than 20% by weight, or no more than 10% by weight, or no more than 5% by weight, or no more than 3% by weight, or no more than 1% by weight, of the amount of compound present in the composition, based on the total weight of the compound in the composition.

For example, in some embodiments, a composition comprising the compound of formula (Ic), or a salt thereof, the (2R,3R) enantiomer makes up at least 50% by weight, or at least 60% by weight, or at least 70% by weight, or at least 80% by weight, or at least 90% by weight, or at least 95% by weight, or at least 97% by weight, or at least 99% by weight, of the amount of compound present in the composition, based on the total weight of the compound [i.e., amount of (2R,3R)+amount of (2S,3R)+amount of (2R,3S)+amount of (2S,3S)] in the composition. In some other embodiments, a composition comprising the compound of formula (Ic), or a salt thereof, the (2R,3S) enantiomer makes up at least 50% by weight, or at least 60% by weight, or at least 70% by weight, or at least 80% by weight, or at least 90% by weight, or at least 95% by weight, or at least 97% by weight, or at least 99% by weight, of the amount of compound present in the composition, based on the total weight of the compound in the composition. In some other embodiments, a composition comprising the compound of formula (Ic), or a salt thereof, the (2S,3R) enantiomer makes up at least 50% by weight, or at least 60% by weight, or at least 70% by weight, or at least 80% by weight, or at least 90% by weight, or at least 95% by weight, or at least 97% by weight, or at least 99% by weight, of the amount of compound present in the composition, based on the total weight of the compound in the composition. In some other embodiments, a composition comprising the compound of formula (Ic), or a salt thereof, the (2S,3S) enantiomer makes up at least 50% by weight, or at least 60% by weight, or at least 70% by weight, or at least 80% by weight, or at least 90% by weight, or at least 95% by weight, or at least 97% by weight, or at least 99% by weight, of the amount of compound present in the composition, based on the total weight of the compound in the composition.

In some other embodiments of any of the embodiments of the preceding paragraph, a composition comprising the compound of formula (Ic), or a salt thereof, the (2R,3R) enantiomer makes up no more than 50% by weight, or no more than 40% by weight, or no more than 30% by weight, or no more than 20% by weight, or no more than 10% by weight, or no more than 5% by weight, or no more than 3% by weight, or no more than 1% by weight, of the amount of compound present in the composition, based on the total weight of the compound in the composition. In some other embodiments of any of the embodiments of the preceding paragraph, a composition comprising the compound of formula (Ic), or a salt thereof, the (2R,3S) enantiomer makes up no more than 50% by weight, or no more than 40% by weight, or no more than 30% by weight, or no more than 20% by weight, or no more than 10% by weight, or no more than 5% by weight, or no more than 3% by weight, or no more than 1% by weight, of the amount of compound present in the composition, based on the total weight of the compound in the composition. In some other embodiments of any of the embodiments of the preceding paragraph, a composition comprising the compound of formula (Ic), or a salt thereof, the (2S,3R) enantiomer makes up no more than 50% by weight, or no more than 40% by weight, or no more than 30% by weight, or no more than 20% by weight, or no more than 10% by weight, or no more than 5% by weight, or no more than 3% by weight, or no more than 1% by weight, of the amount of compound present in the composition, based on the total weight of the compound in the composition. In some other embodiments of any of the embodiments of the preceding paragraph, a composition comprising the compound of formula (Ic), or a salt thereof, the (2S,3S) enantiomer makes up no more than 50% by weight, or no more than 40% by weight, or no more than 30% by weight, or no more than 20% by weight, or no more than 10% by weight, or no more than 5% by weight, or no more than 3% by weight, or no more than 1% by weight, of the amount of compound present in the composition, based on the total weight of the compound in the composition.

Separation of the individual isomers or selective synthesis of the individual isomers is accomplished by application of various methods which are well known to practitioners in the art. Unless otherwise indicated (e.g., where the stereochemistry of a chiral center is explicitly shown), all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

In some embodiments, the compounds disclosed herein are capable of forming acid and/or base salts by virtue of the presence of amino and/or carboxyl groups or groups similar thereto. Physiologically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Physiologically acceptable salts can be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

Uses and Methods

In another aspect, the disclosure provides uses of any flavor-modifying compounds of the foregoing aspects, including any embodiments or combination of embodiments thereof, as set forth above. In certain related aspects, the disclosure provides uses of any flavor-modifying compounds of the foregoing aspects, including any embodiments or combination of embodiments thereof, as set forth above, to enhance the sweetness of an ingestible composition. In some embodiments thereof, the ingestible composition comprises a sweetener, such as a caloric sweetener. In certain other related aspects, the disclosure provides uses of any flavor-modifying compounds of the foregoing aspects, including any embodiments or combination of embodiments thereof, as set forth above, to reduce the sourness of an ingestible composition. In another related aspect, the disclosure provides uses of any flavor-modifying compounds of the foregoing aspects, including any embodiments or combination of embodiments thereof, as set forth above, to reduce the bitterness of an ingestible composition. In certain other related aspects, the disclosure provides uses of any flavor-modifying compounds of the foregoing aspects, including any embodiments or combination of embodiments thereof, as set forth above, in the manufacture of an ingestible composition to enhance the sweetness of the ingestible composition. In some embodiments thereof, the ingestible composition comprises a caloric sweetener. In another related aspect, the disclosure provides uses of any flavor-modifying compounds of foregoing aspects, including any embodiments or combination of embodiments thereof, as set forth above, in the manufacture of an ingestible composition to reduce the sourness of the ingestible composition. In another related aspect, the disclosure provides uses of any flavor-modifying compounds of the foregoing aspects, including any embodiments or combination of embodiments thereof, as set forth above, in the manufacture of an ingestible composition to reduce the bitterness of the ingestible composition.

The disclosure also provides methods that correspond to each of the foregoing uses. Thus, in certain related aspects, the disclosure provides methods of enhancing the sweetness of an ingestible composition, comprising introducing an amount (such as a sweetness-enhancing effective amount) of any flavor-modifying compounds of foregoing aspects, including any embodiments or combination of embodiments thereof, as set forth above, to the ingestible composition. In some other related aspects, the disclosure provides methods of reducing the sourness of an ingestible composition, comprising introducing an amount (such as a sourness-reducing effective amount) of any flavor-modifying compounds of foregoing aspects, including any embodiments or combination of embodiments thereof, as set forth above, to the ingestible composition. In some other related aspects, the disclosure provides methods of reducing the bitterness of an ingestible composition, comprising introducing an amount (such as a bitterness-reducing effective amount) of any flavor-modifying compounds of foregoing aspects, including any embodiments or combination of embodiments thereof, as set forth above, to the ingestible composition.

The foregoing uses and methods generally involve the use of the flavor-modifying compounds in a composition containing one or more additional ingredients. For example, in at least one aspect, the disclosure provides compositions comprising any flavor-modifying compounds of the foregoing aspects, including any embodiments or combination of embodiments thereof, as set forth above, wherein the flavor-modifying compounds make up at least 50% by weight of the compositions on a dry weight basis (e.g., based on the total weight of the composition excluding the weight of any liquid carrier). In a related aspect, the disclosure provides solid-state compositions comprising any flavor-modifying compounds of the foregoing aspects, including any embodiments or combination of embodiments thereof, as set forth above, wherein the flavor-modifying compounds make up at least 50% by weight of the solid-state compositions, based on the total weight of composition. In another related aspect, the disclosure provides ingestible compositions comprising flavor-modifying compounds of the foregoing aspects, including any embodiments or combination of embodiments thereof, as set forth above, wherein the concentration of the flavor-modifying compounds in the ingestible compositions is no more than 200 ppm. In another related aspect, the disclosure provides ingestible compositions comprising any flavor-modifying compounds of the foregoing aspects, including any embodiments or combination of embodiments thereof, as set forth above, wherein the ingestible compositions comprise no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, of steviol glycosides (including rebaudioside A). In another related aspect, the disclosure provides ingestible compositions comprising any flavor-modifying compounds of the foregoing aspects, including any embodiments or combination of embodiments thereof, as set forth above, wherein the ingestible compositions comprise a caloric sweetener, such as sucrose, fructose, xylitol, erythritol, or combinations thereof. In another related aspect, the disclosure provides a concentrated sweetening composition comprising any flavor-modifying compounds of the foregoing aspects, including any embodiments or combination of embodiments thereof, as set forth above, and a sweetener.

In certain embodiments of any aspects and embodiments set forth herein that refer to an ingestible composition, the ingestible composition is a non-naturally-occurring product, such as a composition specifically manufactured for the production of a flavored product, such as food or beverage product.

In general, compounds as disclosed and described herein, individually or in combination, can be provided in a composition, such as an ingestible composition. In one embodiment, compounds as disclosed and described herein, individually or in combination, can impart a more sugar-like temporal profile or flavor profile to a sweetener composition by combining one or more of the compounds as disclosed and described herein with one or more sweeteners in the sweetener composition. In another embodiment, compounds as disclosed and described herein, individually or in combination, can increase or enhance the sweet taste of a composition by contacting the composition thereof with the compounds as disclosed and described herein to form a modified composition.

In certain particular embodiments, the ingestible composition comprises sucrose and the a flavor-modifying compound. In some such embodiments, the introduction of the flavor-modifying compound permits one to use less sucrose (such as more than 10% less, more than 20% less, more than 30% less, more than 40% less, more than 50% less, more than 60% less, or more than 70% less) and still achieve a level of sweetness characteristic of a comparable product that employs more sucrose. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like. The sucrose can be introduced in any suitable form, such as natural syrups (cane syrup) and the like.

In certain particular embodiments, the ingestible composition comprises fructose and a flavor-modifying compound. In some such embodiments, the introduction of the flavor-modifying compound permits one to use less fructose (such as more than 10% less, more than 20% less, more than 30% less, more than 40% less, more than 50% less, more than 60% less, or more than 70% less) and still achieve a level of sweetness characteristic of a comparable product that employs more fructose. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some embodiments, the ingestible composition is a food product, such as any of those specifically listed below. In other embodiments, the ingestible composition is a beverage product, such as a soda, and the like. The fructose can be supplied in any suitable form, such as natural syrups, high-fructose corn syrup, and the like.

In certain particular embodiments, the ingestible composition comprises high-fructose corn syrup and a flavor-modifying compound. In some such embodiments, the introduction of the flavor-modifying compound permits one to use less high-fructose corn syrup (such as more than 10% less, more than 20% less, more than 30% less, more than 40% less, more than 50% less, more than 60% less, or more than 70% less) and still achieve a level of sweetness characteristic of a comparable product that employs more high-fructose corn syrup. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. In some embodiments, the ingestible composition is a food product, such as any of those specifically listed below. In other embodiments, the ingestible composition is a beverage product, such as a soda, and the like.

In certain particular embodiments, the ingestible composition comprises glucose (for example, D-glucose, in either its alpha or beta forms, or a combination thereof) and a flavor-modifying compound. In some such embodiments, the introduction of the flavor-modifying compound permits one to use less glucose (such as more than 10% less, more than 20% less, more than 30% less, more than 40% less, more than 50% less, more than 60% less, or more than 70% less) and still achieve a level of sweetness characteristic of a comparable product that employs more glucose. In some embodiments, the concentration of flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like. The glucose can be introduced in any suitable form, such as natural syrups and the like.

In certain particular embodiments, the ingestible composition comprises sucralose and a flavor-modifying compound. In some such embodiments, the introduction of the flavor-modifying compound permits one to use less sucralose (such as more than 10% less, more than 20% less, more than 30% less, more than 40% less, more than 50% less, more than 60% less, or more than 70% less) and still achieve a level of sweetness characteristic of a comparable product that employs more sucralose. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises rebaudiosides (such as rebaudioside A, rebaudioside D, rebaudioside E, rebaudioside M, or any combination thereof) and a flavor-modifying compound. In some such embodiments, the introduction of the flavor-modifying compound permits one to use less rebaudioside (such as more than 10% less, more than 20% less, more than 30% less, more than 40% less, more than 50% less, more than 60% less, or more than 70% less) and still achieve a level of sweetness characteristic of a comparable product that employs more rebaudioside. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises acefulfame K and a flavor-modifying compound. In some such embodiments, the introduction of the flavor-modifying compound permits one to use less acesulfame K (such as more than 10% less, more than 20% less, more than 30% less, more than 40% less, more than 50% less, more than 60% less, or more than 70% less) and still achieve a level of sweetness characteristic of a comparable product that employs more acesulfame K. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises allulose and a flavor-modifying compound. In some such embodiments, the introduction of the flavor-modifying compound permits one to use less allulose (such as more than 10% less, more than 20% less, more than 30% less, more than 40% less, more than 50% less, more than 60% less, or more than 70% less) and still achieve a level of sweetness characteristic of a comparable product that employs more allulose. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises erythritol and a flavor-modifying compound. In some such embodiments, the introduction of the flavor-modifying compound permits one to use less erythritol (such as more than 10% less, more than 20% less, more than 30% less, more than 40% less, more than 50% less, more than 60% less, or more than 70% less) and still achieve a level of sweetness characteristic of a comparable product that employs more erythritol. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises aspartame and a flavor-modifying compound. In some such embodiments, the introduction of the flavor-modifying compound permits one to use less aspartame (such as more than 10% less, more than 20% less, more than 30% less, more than 40% less, more than 50% less, more than 60% less, or more than 70% less) and still achieve a level of sweetness characteristic of a comparable product that employs more aspartame. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises cyclamate and a flavor-modifying compound. In some such embodiments, the introduction of the flavor-modifying compound permits one to use less cyclamate (such as more than 10% less, more than 20% less, more than 30% less, more than 40% less, more than 50% less, more than 60% less, or more than 70% less) and still achieve a level of sweetness characteristic of a comparable product that employs more cyclamate. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like.

In certain particular embodiments, the ingestible composition comprises a mogroside (such as mogroside III, mogroside IV, mogroside V, siamenoside, isomogroside V, mogroside IVE, isomogroside V, mogroside IIIE, 11-oxomogroside V, the alpha isomer of isomogroside V, and any combinations thereof) and a flavor-modifying compound. In some such embodiments, the introduction of the flavor-modifying compound permits one to use less a mogroside (such as more than 10% less, more than 20% less, more than 30% less, more than 40% less, more than 50% less, more than 60% less, or more than 70% less) and still achieve a level of sweetness characteristic of a comparable product that employs more mogroside. In some embodiments, the concentration of the flavor-modifying compound is no more than 1000 ppm, or no more than 900 ppm, or no more than 800 ppm, or no more than 700 ppm, or no more than 600 ppm, or no more than 500 ppm, or no more than 400 ppm, or no more than 300 ppm, or no more than 200 ppm, or no more than 100 ppm, or no more than 50 ppm, or no more than 25 ppm, or no more than 10 ppm. Such ingestible compositions can be in any suitable form. In some embodiments, the ingestible composition is a food product, such as any of those specifically listed below. In other embodiments, the ingestible composition is a beverage product, such as a soda, and the like. Additional mogroside compounds that may be suitably used are described in U.S. Patent Application Publication No. 2017/0119032.

Thus, in some embodiments, the compositions set forth in any of the foregoing aspects (including in any uses or methods), comprise a flavor-modifying compound and a sweetener. In some embodiments, the composition further comprises a vehicle. In some embodiments, the vehicle is water. In some embodiments, the flavor-modifying compound is present at a concentration at or below its sweetness recognition threshold.

For example, in some embodiments, the sweetener is present in an amount from about 0.1% to about 12% by weight. In some embodiments, the sweetener is present in an amount from about 0.2% to about 10% by weight. In some embodiments, the sweetener is present in an amount from about 0.3% to about 8% by weight. In some embodiments, the sweetener is present in an amount from about 0.4% to about 6% by weight. In some embodiments, the sweetener is present in an amount from about 0.5% to about 5% by weight. In some embodiments, the sweetener is present in an amount from about 1% to about 2% by weight. In some embodiments, the sweetener is present in an amount from about 0.1% to about 5% by weight. In some embodiments, the sweetener is present in an amount from about 0.1% to about 4% by weight. In some embodiments, the sweetener is present in an amount from about 0.1% to about 3% by weight. In some embodiments, the sweetener is present in an amount from about 0.1% to about 2% by weight. In some embodiments, the sweetener is present in an amount from about 0.1% to about 1% by weight. In some embodiments, the sweetener is present in an amount from about 0.1% to about 0.5% by weight. In some embodiments, the sweetener is present in an amount from about 0.5% to about 10% by weight. In some embodiments, the sweetener is present in an amount from about 2% to about 8% by weight. In some further embodiments of the embodiments set forth in this paragraph, the sweetener is sucrose, fructose, glucose, xylitol, erythritol, or combinations thereof.

In some other embodiments, the sweetener is present in an amount from 10 ppm to 1000 ppm. In some embodiments, the sweetener is present in an amount from 20 ppm to 800 ppm. In some embodiments, the sweetener is present in an amount from 30 ppm to 600 ppm. In some embodiments, the sweetener is present in an amount from 40 ppm to 500 ppm. In some embodiments, the sweetener is present in an amount from 50 ppm to 400 ppm. In some embodiments, the sweetener is present in an amount from 50 ppm to 300 ppm. In some embodiments, the sweetener is present in an amount from 50 ppm to 200 ppm. In some embodiments, the sweetener is present in an amount from 50 ppm to 150 ppm. In some further embodiments of the embodiments set forth in this paragraph, the sweetener is a steviol glycoside, a mogroside, a derivative of either of the foregoing, such as glycoside derivatives (e.g., glucosylates), or any combination thereof.

The compositions can include any suitable sweeteners or combination of sweeteners. In some embodiments, the sweetener is a common saccharide sweeteners, such as sucrose, fructose, glucose, and sweetener compositions comprising natural sugars, such as corn syrup (including high fructose corn syrup) or other syrups or sweetener concentrates derived from natural fruit and vegetable sources. In some embodiments, the sweetener is sucrose, fructose, or a combination thereof. In some embodiments, the sweetener is sucrose. In some other embodiments, the sweetener is selected from rare natural sugars including D-allose, D-psicose, L-ribose, D-tagatose, L-glucose, L-fucose, L-arbinose, D-turanose, and D-leucrose. In some embodiments, the sweetener is selected from semi-synthetic "sugar alcohol" sweeteners such as erythritol, isomalt, lactitol, mannitol, sorbitol, xylitol, maltodextrin, and the like. In some embodiments, the sweetener is selected from artificial sweeteners such as aspartame, saccharin, acesulfame-K, cyclamate, sucralose, and alitame. In some embodiments, the sweetener is selected from the group consisting of cyclamic acid, mogroside, tagatose, maltose, galactose, mannose, sucrose, fructose, lactose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A, other sweet Stevia-based glycosides, chemically modified steviol glycosides (such as glucosylated steviol glycosides), mogrosides, chemically modified mogrosides (such as glucosylated mogrosides), carrelame and other guanidine-based sweeteners. In some embodiments, the sweetener is a combination of two or more of the sweeteners set forth in this paragraph. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof. In some embodiments, the sugar may be sucrose. In some embodiments, the sugar may be a combination of fructose and glucose.

The sweetener can also include, for example, sweetener compositions comprising one or more natural or synthetic carbohydrate, such as corn syrup, high fructose corn syrup, high maltose corn syrup, glucose syrup, sucralose syrup, hydrogenated glucose syrup (HGS), hydrogenated starch hydrolyzate (HSH), or other syrups or sweetener concentrates derived from natural fruit and vegetable sources, or semi-synthetic "sugar alcohol" sweeteners such as polyols. Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, isomaltulose, maltodextrin, and the like, and sugar alcohols or any other carbohydrates or combinations thereof capable of being reduced which do not adversely affect taste.

The sweetener may be a natural or synthetic sweetener that includes, but is not limited to, agave inulin, agave nectar, agave syrup, amazake, brazzein, brown rice syrup, coconut crystals, coconut sugars, coconut syrup, date sugar, fructans (also referred to as inulin fiber, fructo-oligosaccharides, or oligo-fructose), green stevia powder, *Stevia rebaudiana*, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, rebaudioside M and other sweet stevia-based glycosides, stevioside, stevioside extracts, honey, Jerusalem artichoke syrup, licorice root, luo han guo (fruit, powder, or extracts), lucuma (fruit, powder, or extracts), maple sap (including, for example, sap extracted from *Acer saccharum, Acer nigrum, Acer rubrum, Acer saccharinum, Acer platanoides, Acer negundo, Acer macrophyllum, Acer grandidentatum, Acer glabrum, Acer mono*), maple syrup, maple sugar, walnut sap (including, for example, sap extracted from *Juglans cinerea, Juglans nigra, Juglans ailatifolia, Juglans regia*), birch sap (including, for example, sap extracted from *Betula papyrifera, Betula alleghaniensis, Betula lenta, Betula nigra, Betula populifolia, Betula pendula*), sycamore sap (such as, for example, sap extracted from *Platanus occidentalis*), ironwood sap (such as, for example, sap extracted from *Ostrya virginiana*), mascobado, molasses (such as, for example, blackstrap molasses), molasses sugar, monatin, monellin, cane sugar (also referred to as natural sugar, unrefined cane sugar, or sucrose), palm sugar, panocha, piloncillo, rapadura, raw sugar, rice syrup, sorghum, sorghum syrup, cassava syrup (also referred to as tapioca syrup), thaumatin, yacon root, malt syrup, barley malt syrup, barley malt powder, beet sugar, cane sugar, crystalline juice crystals, caramel, carbitol, carob syrup, castor sugar, hydrogenated starch hydrolates, hydrolyzed can juice, hydrolyzed starch, invert sugar, anethole, arabinogalactan, arope, syrup, P-4000, acesulfame potassium (also referred to as acesulfame K or ace-K), alitame (also referred to as aclame), advantame, aspartame, baiyunoside, neotame, benzamide derivatives, bernadame, canderel, carrelame and other guanidine-based sweeteners, vegetable fiber, corn sugar, coupling sugars, curculin, cyclamates, cyclocarioside I, demerara, dextran, dextrin, diastatic malt, dulcin, sucrol, valzin, dulcoside A, dulcoside B, emulin, enoxolone, maltodextrin, saccharin, estragole, ethyl maltol, glucin, gluconic acid, glucono-lactone, glucosamine, glucoronic acid, glycerol, glycine, glycyphillin, glycyrrhizin, glycyrrhetic acid monoglucuronide, golden sugar, yellow sugar, golden syrup, granulated sugar, gynostemma, hemandulcin, isomerized liquid sugars, jallab, chicory root dietary fiber, kynurenine derivatives (including N'-formyl-kynurenine, N'-acetyl-kynurenine, 6-chloro-kynurenine), galactitol, litesse, ligicane, lycasin, lugduname, guanidine, falemum, mabinlin I, mabinlin II, maltol, maltisorb, maltodextrin, maltotriol, mannosamine, miraculin, mizuame, mogrosides (including, for example, mogroside IV, mogroside V, and neomogroside), mukurozioside, nano sugar, naringin dihydrochalcone, neohesperidine dihydrochalcone, nib sugar, nigero-oligosaccharide, norbu, orgeat syrup, osladin, pekmez, pentadin, periandrin I, perillaldehyde, perillartine, petphyllum, phenylalanine, phlomisoside I, phlorodizin, phyllodulcin, polyglycitol syrups, polypodoside A, pterocaryoside A, pterocaryoside B, rebiana, refiners syrup, rub syrup, rubusoside, selligueain A, shugr, siamenoside I, siraitia grosvenorii, soybean oligosaccharide, Splenda, SRI oxime V, steviol glycoside, steviolbioside, stevioside, strogins 1, 2, and 4, sucronic acid, sucrononate, sugar, suosan, phloridzin, superaspartame, tetrasaccharide, threitol, treacle, trilobtain, tryptophan and derivatives (6-trifluoromethyl-tryptophan, 6-chloro-D-tryptophan), vanilla sugar, volemitol, birch syrup, aspartame-acesulfame, assugrin, and combinations or blends of any two or more thereof.

In still other embodiments, the sweetener can be a chemically or enzymatically modified natural high potency sweetener. Modified natural high potency sweeteners include glycosylated natural high potency sweetener such as glucosyl-, galactosyl-, or fructosyl-derivatives containing 1-50 glycosidic residues. Glycosylated natural high potency sweeteners may be prepared by enzymatic transglycosylation reaction catalyzed by various enzymes possessing transglycosylating activity. In some embodiments, the modified sweetener can be substituted or unsubstituted.

Additional sweeteners also include combinations of any two or more of any of the aforementioned sweeteners. In some embodiments, the sweetener may comprise combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a caloric sweetener, such as sucrose, fructose, xylitol, erythritol, or combinations thereof. In some embodiments, the ingestible compositions are free (or, in some embodiments) substantially free of stevia-derived sweeteners, such as steviol glycosides, glucosylated steviol glycosides, or rebaudiosides. For example, in some embodiments, the ingestible compositions are either free of stevia-derived sweeteners or comprise stevia-derived sweeteners in a concentration of no more than 1000 ppm, or no more than 500 ppm, or no more than 200 ppm, or no more than 100 ppm, or no more than 50 ppm, or no more than 20 ppm, or no more than 10 ppm, or no more than 5 ppm, or no more than 3 ppm, or no more than 1 ppm.

The flavor-modifying compounds can be present in the ingestible compositions in any suitable amount. In some embodiments, the flavor-modifying compounds are present in an amount sufficient to enhance the taste (e.g., enhance the sweetness, reduce the sourness, or reduce the bitterness) of the compositions. Thus, in some embodiments, the ingestible composition comprises the flavor-modifying compound in a concentration no greater than 200 ppm, or no greater than 150 ppm, or no greater than 100 ppm, or no greater than 50 ppm, or no greater than 40 ppm, or no greater than 30 ppm, or no greater than 20 ppm. In some embodiments, the flavor-modifying compound is present in a minimum amount, such as 1 ppm or 5 ppm. Thus, in some embodiments, the ingestible composition comprises the flavor-modifying compound in a concentration ranging from 1 ppm to 200 ppm, or from 1 ppm to 150 ppm, or from 1 ppm to 100 ppm, or from 1 ppm to 50 ppm, or from 1 ppm to 40 ppm, or from 1 ppm to 30 ppm, or from 1 ppm to 20 ppm, or from 5 ppm to 200 ppm, or from 5 ppm to 150 ppm, or from 5 ppm to 100 ppm, or from 5 ppm to 50 ppm, or from 5 ppm to 40 ppm, or from 5 ppm to 30 ppm, or from 5 ppm to 20 ppm. In embodiments where a sweetener, such as sucrose or fructose, are present, the weight-to-weight ratio of sweetener to the flavor-modifying compound in the ingestible composition ranges from 1000:1 to 50000:1, or from 1000:1 to 10000:1, or from 2000:1 to 8000:1.

The ingestible compositions or sweetener concentrates can, in certain embodiments, comprise any additional ingredients or combination of ingredients as are commonly used in food and beverage products, including, but not limited to:

- acids, including, for example citric acid, phosphoric acid, ascorbic acid, sodium acid sulfate, lactic acid, or tartaric acid;
- bitter ingredients, including, for example caffeine, quinine, green tea, catechins, polyphenols, green robusta coffee extract, green coffee extract, potassium chloride, menthol, or proteins (such as proteins and protein isolates derived from plants, algae, or fungi);
- coloring agents, including, for example caramel color, Red #40, Yellow #5, Yellow #6, Blue #1, Red #3, purple carrot, black carrot juice, purple sweet potato, vegetable juice, fruit juice, beta carotene, turmeric curcumin, or titanium dioxide;
- preservatives, including, for example sodium benzoate, potassium benzoate, potassium sorbate, sodium metabisulfate, sorbic acid, or benzoic acid;
- antioxidants including, for example ascorbic acid, calcium disodium EDTA, alpha tocopherols, mixed tocopherols, rosemary extract, grape seed extract, resveratrol, or sodium hexametaphosphate;
- vitamins or functional ingredients including, for example resveratrol, Co-Q10, omega 3 fatty acids, theanine, choline chloride (citocoline), fibersol, inulin (chicory root), taurine, panax ginseng extract, guanana extract, ginger extract, L-phenylalanine, L-carnitine, L-tartrate, D-glucoronolactone, inositol, bioflavonoids, Echinacea, ginko biloba, yerba mate, flax seed oil, garcinia cambogia rind extract, white tea extract, ribose, milk thistle extract, grape seed extract, pyrodixine HCl (vitamin B6), cyanoobalamin (vitamin B12), niacinamide (vitamin B3), biotin, calcium lactate, calcium pantothenate (pantothenic acid), calcium phosphate, calcium carbonate, chromium chloride, chromium polynicotinate, cupric sulfate, folic acid, ferric pyrophosphate, iron, magnesium lactate, magnesium carbonate, magnesium sulfate, monopotassium phosphate, monosodium phosphate, phosphorus, potassium iodide, potassium phosphate, riboflavin, sodium sulfate, sodium gluconate, sodium polyphosphate, sodium bicarbonate, thiamine mononitrate, vitamin D3, vitamin A palmitate, zinc gluconate, zinc lactate, or zinc sulphate;
- clouding agents, including, for example ester gun, brominated vegetable oil (BVO), or sucrose acetate isobutyrate (SAIB);
- buffers, including, for example sodium citrate, potassium citrate, or salt;
- flavors, including, for example propylene glycol, ethyl alcohol, glycerine, gum Arabic (gum acacia), maltodextrin, modified corn starch, dextrose, natural flavor, natural flavor with other natural flavors (natural flavor WONF), natural and artificial flavors, artificial flavor, silicon dioxide, magnesium carbonate, or tricalcium phosphate; or
- starches and stabilizers, including, for example pectin, xanthan gum, carboxylmethylcellulose (CMC), polysorbate 60, polysorbate 80, medium chain triglycerides, cellulose gel, cellulose gum, sodium caseinate, modified food starch, gum Arabic (gum acacia), inulin, or carrageenan.

The ingestible compositions or sweetener concentrates can have any suitable pH. In some embodiments, the flavor-modifying compounds enhance the sweetness of a sweetener under a broad range of pH, e.g., from lower pH to neutral pH. The lower and neutral pH includes, but is not limited to, a pH from about 2.5 to about 8.5; from about 3.0 to about 8.0; from about 3.5 to about 7.5; and from about 4.0 to about 7. In certain embodiments, compounds as disclosed and described herein, individually or in combination, can enhance the perceived sweetness of a fixed concentration of a sweetener in taste tests at a compound concentration of about 50 μM, 40 μM, 30 μM, 20 μM, or 10 μM at both low to neutral pH value. In certain embodiments, the enhancement factor of the compounds as disclosed and described herein, individually or in combination, at the lower pH is substantially similar to the enhancement factor of the compounds at neutral pH. Such consistent sweet enhancing property under a broad range of pH allow a broad use in a wide variety of foods and beverages of the compounds as disclosed and described herein, individually or in combination.

The ingestible compositions set forth according to any of the foregoing embodiments, also include, in certain embodiments, one or more additional flavor-modifying compounds, such as compounds that enhance sweetness (e.g., hesperetin, neohesperitin, phloretin, naringenin, glucosylated steviol glycosides, etc.), compounds that block bitterness, compounds that enhance umami, compounds that reduce sourness or licorice taste, compounds that enhance saltiness, compounds that enhance a cooling effect, or any combinations of the foregoing.

The ingestible compositions set forth according to any of the foregoing embodiments, also include, in certain embodiments, one or more additional flavor-modifying compounds, such as compounds that enhance sweetness (e.g., hesperetin, naringenin, glucosylated steviol glycosides, etc.), compounds that block bitterness, compounds that enhance umami, compounds that reduce sourness or licorice taste, compounds that enhance saltiness, compounds that enhance a cooling effect, or any combinations of the foregoing.

Thus, in some embodiments, ingestible compositions disclosed herein comprise a flavor-modifying compound according to any of the embodiments or combination of embodiments set forth above, are combined with one or more other sweetness enhancing compounds. Such sweetness enhancing compounds include, but are not limited to, naturally derived compounds, such as hesperitin, naringenin, glucosylated steviol glycosides, or synthetic compounds, such as any compounds set forth in U.S. Pat. Nos. 8,541,421;

8,815,956; 9,834,544; 8,592,592; 8,877,922; 9,000,054; and 9,000,051, as well as U.S. Patent Application Publication No. 2017/0119032. The flavor-modifying compound may be used in combination with such other sweetness enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1. In some embodiments of any of the preceding embodiments, the flavor-modifying compound is combined with glucosylated steviol glycosides in any of the above ratios. As used herein, the term "glucosylated steviol glycoside" refers to the product of enzymatically glucosylating natural steviol glycoside compounds. The glucosylation generally occurs through a glycosidic bond, such as an α-1,2 bond, an α-1,4 bond, an α-1.6 bond, a β-1,2 bond, a β-1,4 bond, a β-1,6 bond, and so forth. In some embodiments of any of the preceding embodiments, the TM1 compound (or any comestibly acceptable salts thereof) is combined with N-(1-((4-amino-2,2-dioxo-1H-benzo[c][1,2,6]thiadiazin-5-yl)oxy)-2-methyl-propan-2-yl)isonicotinamide, in any of the above ratios.

In some further embodiments, ingestible compositions disclosed herein comprise a flavor-modifying compound according to any of the embodiments or combination of embodiments set forth above, are combined with one or more umami enhancing compounds. Such umami enhancing compounds include, but are not limited to, naturally derived compounds, such as ericamide, or synthetic compounds, such as any compounds set forth in U.S. Pat. Nos. 8,735,081; 8,124,121; and 8,968,708. The flavor-modifying compound may be used in combination with such umami enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1,20:1,21:1,22:1,23:1,24:1, or 25:1.

In some further embodiments, ingestible compositions disclosed herein comprise a flavor-modifying compound according to any of the embodiments or combination of embodiments set forth above, are combined with one or more cooling enhancing compounds. Such cooling enhancing compounds include, but are not limited to, naturally derived compounds, such as menthol or analogs thereof, or synthetic compounds, such as any compounds set forth in U.S. Pat. Nos. 9,394,287 and 10,421,727. The flavor-modifying compound may be used in combination with such umami enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1,20:1,21:1, 22:1,23:1,24:1, or 25:1.

In some further embodiments, ingestible compositions disclosed herein comprise a flavor-modifying compound according to any of the embodiments or combination of embodiments set forth above, are combined with one or more bitterness blocking compounds.

Such bitterness blocking compounds include, but are not limited to, naturally derived compounds, such as menthol or analogs thereof, or synthetic compounds, such as any compounds set forth in U.S. Pat. Nos. 8,076,491; 8,445,692; and 9,247,759. The flavor-modifying compound may be used in combination with such bitterness blockers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1,2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein comprise a flavor-modifying compound according to any of the embodiments or combination of embodiments set forth above, are combined with one or more sour taste modulating compounds. The flavor-modifying compound may be used in combination with such sour taste modulating compounds in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein comprise a flavor-modifying compound according to any of the embodiments or combination of embodiments set forth above, are combined with one or more mouthfeel modifying compounds. Such mouthfeel modifying compounds include, but are not limited to, tannins, cellulosic materials, bamboo powder, and the like. The flavor-modifying compound may be used in combination with such mouthfeel enhancers in any suitable ratio (w/w) ranging from 1:1000 to 1000:1, or from 1:100 to 100:1, or fro, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1,20:1,21:1,22:1,23:1,24:1, or 25:1.

In some further embodiments, ingestible compositions disclosed herein comprise a flavor-modifying compound according to any of the embodiments or combination of embodiments set forth above, are combined with one or more flavor masking compounds. Such flavor masking compounds include, but are not limited to, cellulosic materials, materials extracted from fungus, materials extracted from plants, citric acid, carbonic acid (or carbonates), and the like. The flavor-modifying compound may be used in combination with such mouthfeel enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some aspects related to the preceding aspects and embodiments, the disclosure provides uses of the flavor-modifying compound to enhance the flavor of a flavored composition, such as a flavored article. Such flavored compositions can use any suitable flavors, such as any of the flavors set forth above.

Flavored Products and Concentrates

In certain aspects, the disclosure provides flavored products comprising any compositions of the preceding five aspects. In some embodiment, the flavored products are beverage products, such as soda, flavored water, tea, and the like. In some other embodiments, the flavored products are food products, such as yogurt.

In embodiments where the flavored product is a beverage, the beverage may be selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the beverage may be a soft drink.

In certain embodiments of any aspects and embodiments set forth herein that refer to an flavored product, the flavored product is a non-naturally-occurring product, such as a packaged food or beverage product.

Further non-limiting examples of food and beverage products or formulations include sweet coatings, frostings, or glazes for such products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, burrs, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for flavored products, particularly food and beverage products or formulations, are provided as follows. Exemplary ingestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary ingestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary ingestible compositions also include breakfast cereals, sweet beverages or solid or liquid concentrate compositions for preparing beverages, ideally so as to enable the reduction in concentration of previously known saccharide sweeteners, or artificial sweeteners.

Some embodiments provide a chewable composition that may or may not be intended to be swallowed. In some embodiments, the chewable composition may be gum, chewing gum, sugarized gum, sugar-free gum, functional gum, bubble gum including compounds as disclosed and described herein, individually or in combination.

Typically at least a sweet receptor modulating amount, a sweet receptor ligand modulating amount, a sweet flavor modulating amount, a sweet flavoring agent amount, a sweet flavor enhancing amount, or a therapeutically effective amount of one or more of the present compounds will be added to the ingestible composition, optionally in the presence of sweeteners so that the sweet flavor modified ingestible composition has an increased sweet taste as compared to the ingestible composition prepared without the compounds of the present invention, as judged by human beings or animals in general, or in the case of formulations testing, as judged by a majority of a panel of at least eight human taste testers, via procedures commonly known in the field.

In some embodiments, compounds as disclosed and described herein, individually or in combination, modulate the sweet taste or other taste properties of other natural or synthetic sweet tastants, and ingestible compositions made therefrom. In one embodiment, the compounds as disclosed and described herein, individually or in combination, may be used or provided in its ligand enhancing concentration(s). For example, the compounds as disclosed and described herein, individually or in combination, may be present in an amount of from 0.001 ppm to 100 ppm, or narrower alternative ranges from 0.1 ppm to 50 ppm, from 0.01 ppm to 40 ppm, from 0.05 ppm to 30 ppm, from 0.01 ppm to 25 ppm, or from 0.1 ppm to 30 ppm, or from 0.1 ppm to 25 ppm, or from 1 ppm to 30 ppm, or from 1 ppm to 25 ppm.

In some embodiments, flavor-modifying compounds as disclosed and described herein, individually or in combination, may be provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacturer in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

The flavored products set forth according to any of the foregoing embodiments, also include, in certain embodiments, one or more additional flavor-modifying compounds, such as compounds that enhance sweetness (e.g., hesperetin, naringenin, glucosylated steviol glycosides, etc.), compounds that block bitterness, compounds that enhance umami, compounds that reduce sourness, compounds that enhance saltiness, compounds that enhance a cooling effect, or any combinations of the foregoing.

In certain embodiments of any aspects and embodiments set forth herein that refer to a sweetening or flavoring concentrate, the sweetening or flavoring concentrate is a non-naturally-occurring product, such as a composition specifically manufactured for the production of a flavored product, such as food or beverage product.

In one embodiment, the flavoring concentrate formulation comprises i) compounds as disclosed and described herein, individually or in combination; ii) a carrier; and iii) optionally at least one adjuvant. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the content of which is hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. In some embodiments, the present flavoring concentrate formulation can be carbonated or non-carbonated.

The flavoring concentrate formulation may further comprise a freezing point depressant, nucleating agent, or both as the at least one adjuvant. The freezing point depressant is an ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes an ingestibly acceptable compound or agent which is able to facilitate nucleation. The presence of nucleating agent in the flavoring concentrate formulation can improve the mouthfeel of the frozen Blushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

The sweetening or flavoring concentrates set forth according to any of the foregoing embodiments, also include, in certain embodiments, one or more additional flavor-modifying compounds, such as compounds that enhance sweetness (e.g., hesperetin, naringenin, glucosylated steviol glycosides, etc.), compounds that block bitterness (e.g., eriodictyol, homoeriodictyol, sterubin, and salts or glycoside derivatives thereof, as well as vanillyl lignans, e.g., matairesinol and other compounds set forth in PCT Publication No. WO 2012/146584), compounds that enhance umami (e.g., rubemamine, rubescenamine, (E)-3-(3,4-dimethoxyphenyl)-N-(4-methoxyphenethyl)acrylamide, and the like), compounds that reduce sourness and/or licorice taste, compounds that enhance saltiness, compounds that enhance a cooling effect, or any combinations of the foregoing.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary or desirable to protect sensitive or reactive groups on any of the molecules concerned.

In certain aspects, the disclosure provides methods of making flavor-modifying compounds of the foregoing aspects via an enzyme-catalyzed process. For example, in certain embodiments, the methods include providing a precursor, which is a flavanone, or a derivative thereof, having a hydrogen atom at the 3-position of the central flavanone bicyclic ring system. Suitable non-limiting examples of flavanone precursors include hesperetin, naringenin, eriodictyol, homoeriodictyol, sterubin, or any salts or glycosides thereof. In certain embodiments, the methods include reacting the flavanone precursor with one or more enzymes to provide a non-hydrogen substituent at the 3-position of the central flavanone bicyclic ring system to provide a 3-position-functionalized flavanone compound. In some embodiments, the one or more enzymes provide the functionalization in a specific stereochemistry, such as R or S. The one or more enzymes can provide any suitable functionalization. In some embodiments, the one or more enzymes provide a hydroxyl (—OH) group at the 3-position. In some embodiments, this functionalization can be carried out by the enzyme flavanone 3-hydroxylase. In some embodiments, the 3-position-functionalized flavanone compound van be further functionalized at the 3-positon. For example, in some embodiments where the 3-position-functionalized flavanone compound has a hydroxyl group at the 3-position, the hydroxyl group can be further functionalized using any reagent suitable to react with a hydroxyl group. For example, in some such embodiments, the hydroxyl group at the 3-position is reacted with a carboxylic acid, such as acetic acid, to form an ester (e.g., an acetate). In some such embodiments, the further functionalization is carried out in a way that preserves the absolute stereochemistry at the 3-position.

In some particular embodiments of the foregoing, the methods include providing naringenin (for example, in a suitable solvent system); reacting the naringenin with flavanone 3-hydroxylase to form aromadendrin [(2R,3R)-3,5,7,4'-tetrahydroxyflavanone]; and reacting the aromadendrin with acetic acid (or an ester thereof) to form aromadendrin-3-O-acetate [(2R,3R)-3-acetoxy-5,7,4'-trihydroxyflavanone].

EXAMPLES

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Example 1—Sweetness Enhancement

A test compound, (2R,3R)-3-acetoxy-5,7,4'-trihydroxy-flavanone (A01), was tested in comparison to naringenin for its sweetness enhancement of a 5% (w/w) aqueous solution of sucrose. Taste panelists were asked to taste the following 5% sucrose solutions in Henniez water and rate their sweetness on a scale from 0 to 10, and to rate the presence of any licorice taste in the sample on a scale from 0 to 10. Results are set forth in Table 1.

TABLE 1

| Enhancement | Sweetness (0-10) | Licorice Taste (0-10) |
|---|---|---|
| No flavor modifier/enhancer | 5.0 | 0.0 |
| +50 ppm naringenin | 5.8 | 0.5 |
| +10 ppm A01 | 8.0 | 2.0 |
| +5 ppm A01 | 7.0 | 1.0 |

Example 2—Sweetness Enhancement

The test compound A01 was tested in comparison to other sweetness enhancers in a similar test to that set forth in Example 1. Results are set forth in Table 2. The comparative compounds are taxifolin 3-O-acetate (A02), and ampelopsin 3-O-acetate (A03).

TABLE 2

| Enhancement | Sweetness (0-10) | Licorice Taste (0-10) |
|---|---|---|
| No flavor modifier/enhancer | 5.0 | 0.0 |
| +20 ppm A01 | 8.8 | 1.5 |
| +20 ppm A02 | 6.8 | 2.0 |
| +20 ppm A03 | 5.1 | 0.0 |

Example 3—Sweetener Replacement Testing

The test compound A01 was used in combination with certain sweeteners obtain a comparable sweetness profile to a comparable beverage containing a higher concentration of the sweetener and no amount of test compound A01.

In one test, 45 panelists were asked to select between a beverage sweetened with 450 ppm rebaudioside M and a beverage with 300 ppm rebaudioside M and 12 ppm test compound A01. Of the 45 panelists, 23 selected the former, and 22 selected the latter, which is a statistical equivalence. This demonstrated that introduction of 12 ppm of test compound A01 can permit reduction in concentration of rebaudioside M by 33%.

In another test, 45 panelists were asked to select between a beverage sweetened with 160 ppm sucralose and a beverage with 120 ppm sucralose and 12 ppm test compound A01. Of the 45 panelists, 22 selected the former, and 23 selected the latter, which is a statistical equivalence. This demonstrated that introduction of 12 ppm of test compound A01 can permit reduction in concentration of sucralose by 25%.

Example 4—Compound Preparation by Biotransformation and Chemical Synthesis

The description below sets forth a non-limiting method by which the compound A01 was obtained.

Protein Production

The gene (GenBank: U33932) encoding the flavanone-3-hydroxylase (F3H) from *Arabidopsis thaliana* was ordered with its original gene sequence (only removing an Xho restriction site) and codon-optimised for *E. coli* with and without N-terminal Trx Tag from Twist cloned into pET29a via the restriction sites NcoI and XhoI. *E. coli* BL21Star (DE3) was transformed with the four constructs.

For the precultures 7 mL LB medium containing kanamycin (50 µg/mL) were inoculated with *E. coli* BL21Star (DE3) strains harbouring the constructs and incubated at 37° C. and 200 rpm overnight. Five mL of the precultures were used to inoculate the main culture of 400 mL LB medium containing kanamycin (50 µg/mL), which was incubated at 37° C. until the optical density at 600 nm (OD600) reached approximately 0.8. Expression of AthF3H was induced by 0.1 mM IPTG (isopropyl-D-thiogalactopyranoside) and the cultures were shaken at 20° C. for 20 h. The cells were harvested by centrifugation, and then resuspended in 100 mM potassium phosphate buffer (KPi, pH 7) to an OD of 50. Protein production was confirmed by SDS-PAGE, which showed that AthF3H was very well expressed as soluble protein and no difference between the four constructs.

Biotransformation

Biotransformation were carried out with whole cells of *E. coli* BL21Star(DE3)-AthF3H at OD10 in a total volume of 150 mL in 50 mM Tris/HCl, pH 7, containing 10% MeOH, 4 mM (±)-naringenin, 10 mM α-ketoglutarate, 10 mM ascorbic acid and 0.25 mM $FeSO_4$ at 30° C. for 3 h. The biomass was removed by centrifugation.

Purification of Aromadendrin and Unreacted Naringenin

The supernatant of the biotransformation was poured onto a pre-conditioned Waters Oasis HLB SPE cartridge (6 g). The retention was complete and the cartridge was rinsed with water. Then it was successfully eluted by three volumes of 100 mL of $H_2O$/EtOH, 50:50 (Fr.1-3) and three volumes of $H_2O$/EtOH, 30:70 (Fr.4-6). Fractions 1 and 2 were filtered, pooled, evaporated and then freeze-dried to give 102 mg of 90% pure aromadendrin (molar yield 59%). Similarly fractions 4 and 5 yielded about 60 mg which was pure unreacted naringenin. The measurement of optical rotation of $\alpha_D$=+21° (c=0.5 g/100 mL, EtOH) showed that unreacted naringin was (2R)-(+)-naringenin. Similarly the produced aromadendrin displayed $\alpha_D$=+9° (c=0.5 g/100 mL, EtOH) showing that the major product was of (2R, 3R) configuration.

Synthesis of Aromadendrin-3-O-Acetate

Aromadendrin (100 mg) and 10 mg of dimethylamino-pyridine (DMAP) were diluted in pyridine (10 mL). Acetic anhydride (1 mL) was added drop wise. The reaction was stirred for 15 min. Pyridine was evaporated and the reaction was taken in 100 mL of EtOAc, washed with 5% $KHSO_4$ and brine. It was dried over sodium sulfate and evaporated. The crude product was diluted in 10 mL of $CH_2Cl_2$ and cooled to 0° C. Pyrolidine (500 μL) was added by portions of 100 μL and the reaction was stirred at 0-10° C. for 2 h. Dichloromethane (30 mL) was added and the organic phase was successively washed with 5% $KHSO_4$ and water. The water phase was extract two times with $CH_2Cl_2$. The combined organic phases were dried over sodium sulfate and evaporated. The crude product was purified by flash chromatography over Lichroprep RP-18 (glass column of 45 g) using a gradient of water/acetonitrile 0.1% formic acid (20%, 5 min then 20-80% B in 20 min). The fractions containing the expected product were combined, evaporated and freeze-dried to yield 53 mg of aromadendrin-3-O-acetate (59% yield). The measurement of optical rotation of $\alpha_D$=+22.1° (c=0.5 g/100 mL, EtOH) showed that the product (2R,3R)-(+)-aromadendrin-3-O-acetate. NMR $^{13}C$ (MeOD, 500 MHz): 20.2 (q); 73.8 (d); 82.5 (d); 96.6 (d); 97.7 (d); 102.2 (s); 116.3 (d); 127.9 (s); 130.2 (d); 159.7 (s); 164.3 (s); 165.5 (s); 169.1 (s); 170.9 (s); 193.4 (s).

Example 5—Natural Mixture Testing

In some instances, it may be desirable to obtain the compound A01 from natural sources, where it may be extracted as a mixture with other flavonoid compounds.

Hydrolysis of *Engelhardtia Roxburghiana* Extract

In a 500 mL three necked round bottom flask, fitted with a mechanic stirrer and a condenser, 25 g of *Engelhardtia Roxburhiana* extract (80% astilbin, supplier Xi'an Tuofeng Biotech Ltd.), 250 mL of 1M citric acid (freshly prepared) and 250 mg of Vitamine E were refluxed and stirred overnight night. After cooling, the reaction mixture was extracted 2× with ethyl acetate. Combined organic layers were washed 1× with deionized water, 1× with brine, dried over sodium sulfate, filtered and evaporated to afford 14.4 g of crude *Engelhardtia* hydrolyzate (88.3% yield).

Acetylation of *Engelhardtia* Hydrolysate by Reactive Distillation

In a 500 mL three necked round bottom flask, fitted with a Vigreux 15 cm, a distillation bridge and a magnetic stirrer, 10 g of crude *Engelhardtia* hydrolysate, 200 mL of AcOH and ca 100 mg of Vitamine E were refluxed for 50 h. Acetic acid was subsequently distilled and the reaction mixture was diluted in ~200 mL of ethyl acetate. The organic phase was washed with 200 mL of 5% sodium bicarbonate, 1× with water, 1× with brine, dried over sodium sulfate, filtered and evaporated to give 10 g of yellow-brown powder (87.5% yield).

Quantification of Flavonoids

The UPLC instrument was a Waters Acquity I-Class UPLC system composed of a binary pump, a PDA detector, a column manager (4 columns), a fixed loop sample manager and an ELSD detector. The mass spectrometer was a QExactive Plus (Thermo). This instrument was calibrated using Thermo infusion solutions not more than 2 weeks ago. The method 4-P-FS-Engelhardtia-MeOH (described above) was used. For quantification, ions 305.0654 (1), 289.0706 (2), 347.0761 (3), 331.0815 (4) were used to give a quadratic calibration curve. The UV range used was 270-320 nm to give a linear calibration curve. The samples were prepared by dissolving exactly 10.88 mg of 1, 10.15 mg of 2, 10.13 mg of 2 and 10.05 mg of 4 in 10.0 mL ethanol; then the stock solution was diluted ten times in ethanol and this solution was the highest point of our calibration curve. This solution at 100 ppm was then diluted to make six points of calibration over a range of 100 ppm to 1 ppm (100:50:25:10:5:1). About-exactly 10.0 mg of the resulting mixture was diluted into 10.0 mL of ethanol. This solution was diluted 5× for quantification (approx. 200 ppm). Table 3 shows the composition of certain flavonoids in the resulting mixture.

TABLE 3

| Compound | % UV |
|---|---|
| Taxifolin 1 | 12.3% |
| Aromadendrin 2 | 7.5% |
| Taxifolin 3-OAc 3 | 41.5% |
| Aromadendrin 3-OAc 4 (Compound A01) | 20.0% |

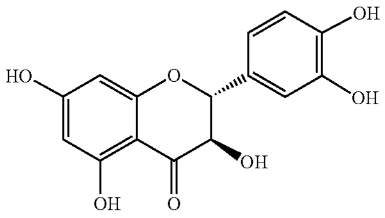

Taxifolin

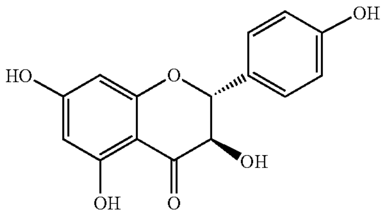

Aromadendrin

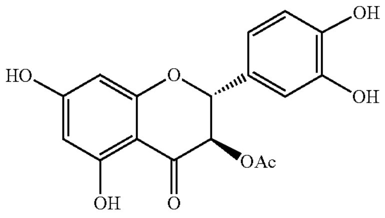

Taxifolin-3-acetate

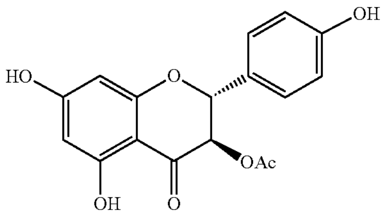

Aromadendrin-3-acetate

Sensory Evaluation

The resulting mixture was introduced into water containing 5% sucrose, the mixture at 50 ppm was about as sweet as pure compound A01 at 20 ppm.

Example 6—Sweetness Enhancement

A test compound, (2R,3R)-3-acetoxy-5,7,3'-trihydroxy-4'-methoxyflavanone (A02), was tested for sweetness enhancement and as a sweetener.

In one test, taste panelists were asked to select between a beverage sweetened with to 9 Bx with sucrose and a beverage sweetened to 7 Bx with sucrose and 2.5 ppm of test compound A02. The panelists perceived the two beverages to have equivalent sweetened. This demonstrated that introduction of 2.5 ppm of test compound A02 can permit reduction in concentration of sucrose by 2 Bx.

In another test, taste panelists were asked to select between a beverage sweetened with 200 ppm rebaudioside M and 10 ppm of test compound A02 and a beverage sweetened to 10 Bx with sucrose. The panelists selected the former beverage to taste sweeter, and found that the combination of rebaudioside M and test compound A02 to impart a natural-tasting sweetness similar to a beverage sweetened with sucrose to 12 Bx.

The invention claimed is:

1. A method of enhancing a sweet taste, or reducing a bitter taste, of an ingestible composition, the method comprising introducing a combination of flavor-modifying compounds to the ingestible composition; wherein the ingestible composition is free of any steviol glycosides; and wherein the combination of flavor-modifying compounds comprises a compound of formula (Ib)

(Ib)

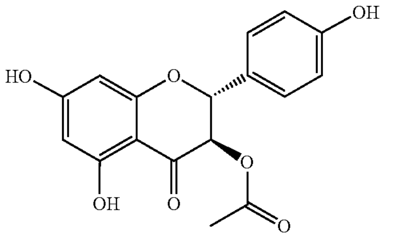

or a salt thereof; and

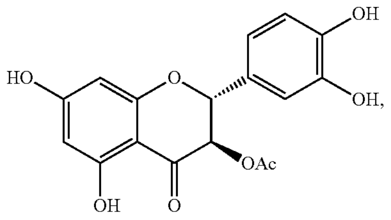 [SMILES: CC(=O)O[C@H]1C(=O)c2c(O)cc(O)cc2O[C@@H]1c1ccc(O)c(O)c1]

or a salt thereof;

wherein the combination of flavor-modifying compounds is present in the ingestible composition at a concentration ranging from 1 ppm to 50 ppm by weight of the ingestible composition; and wherein the ingestible composition comprises a sweetener selected from the group consisting of sucrose, fructose, glucose, and any combination thereof;

wherein the combination of flavor-modifying compounds further comprises

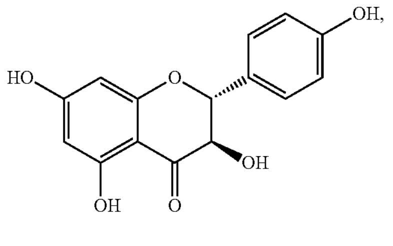 [SMILES: O=C1c2c(O)cc(O)cc2O[C@H](c2ccc(O)cc2)[C@H]1O]

or a salt thereof.

2. The method of claim 1, wherein the combination of flavor-modifying compounds further comprises

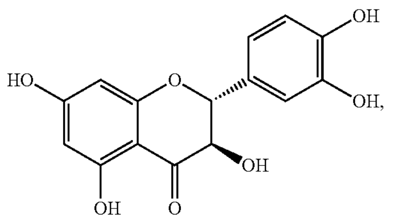 [SMILES: O=C1c2c(O)cc(O)cc2O[C@H](c2ccc(O)c(O)c2)[C@H]1O]

or a salt thereof.

3. An ingestible composition, which comprises a combination of flavor-modifying compounds and a sweetener selected from the group consisting of sucrose, fructose, glucose, and any combination thereof; wherein the combination of flavor-modifying compounds is present at a concentration ranging from 1 ppm to 50 ppm by weight of the ingestible composition, wherein the ingestible composition is free of any steviol glycosides, and wherein the flavor-modifying compound comprises a compound of formula (Ib)

(Ib)

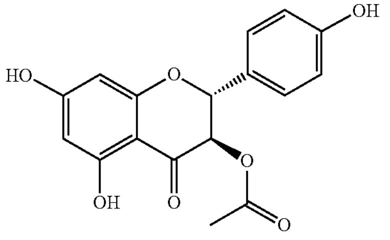

or a salt thereof; and

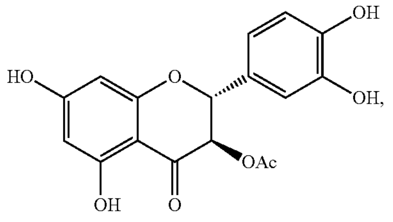 [SMILES: CC(=O)O[C@H]1C(=O)c2c(O)cc(O)cc2O[C@@H]1c1ccc(O)c(O)c1]

or a salt thereof;

wherein the combination of flavor-modifying compounds further comprises
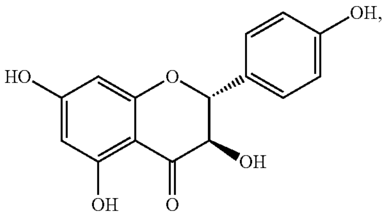 [SMILES: O=C1c2c(O)cc(O)cc2O[C@H](c2ccc(O)cc2)[C@H]1O]
or a salt thereof.
4. The composition of claim 3, wherein the combination of flavor-modifying compounds further comprises
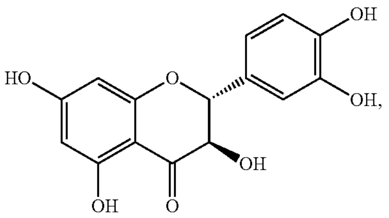 [SMILES: O=C1c2c(O)cc(O)cc2O[C@H](c2ccc(O)c(O)c2)[C@H]1O]
or a salt thereof.
* * * * *